US008666762B2

(12) United States Patent
Kasprisin et al.

(10) Patent No.: US 8,666,762 B2
(45) Date of Patent: Mar. 4, 2014

(54) TISSUE MANAGEMENT SYSTEM

(75) Inventors: Duke O Kasprisin, South Burlington, VT (US); Paul E. Kozloski, Wayzata, MN (US); Susan A. Kozloski, Wayzata, MN (US); Agnes Vercillo, Cicero, NY (US); Jeffrey K. Winstead, Fishers, IN (US)

(73) Assignee: Biomedical Synergies, Inc., Wayzata, MN (US)

( * ) Notice: Subject to any disclaimer, the term of this patent is extended or adjusted under 35 U.S.C. 154(b) by 1321 days.

(21) Appl. No.: 11/584,357

(22) Filed: Oct. 20, 2006

(65) Prior Publication Data

US 2008/0077433 A1 Mar. 27, 2008

Related U.S. Application Data

(63) Continuation-in-part of application No. 11/540,884, filed on Sep. 29, 2006.

(60) Provisional application No. 60/826,492, filed on Sep. 21, 2006.

(51) Int. Cl.
*G06Q 10/00* (2012.01)
*G06Q 50/00* (2012.01)

(52) U.S. Cl.
USPC .................................. 705/2; 705/3

(58) Field of Classification Search
USPC ................................................. 705/2
See application file for complete search history.

(56) References Cited

U.S. PATENT DOCUMENTS

| 5,416,029 | A | 5/1995 | Miller et al. |
| 5,842,179 | A | 11/1998 | Beavers et al. |
| 6,512,459 | B2 | 1/2003 | Benezech et al. |
| 6,539,360 | B1 | 3/2003 | Kadaba |
| 6,861,954 | B2 | 3/2005 | Levin |
| 7,363,167 | B2 * | 4/2008 | Csore et al. ............ 702/19 |
| 2001/0037220 | A1 | 11/2001 | Merry et al. |
| 2002/0049650 | A1 | 4/2002 | Reff |
| 2002/0082957 | A1 | 6/2002 | Krassi |
| 2002/0143580 | A1 | 10/2002 | Bristol et al. |
| 2003/0120633 | A1 | 6/2003 | Torre-Bueno |
| 2003/0175242 | A1 * | 9/2003 | Gruenberg ............ 424/93.2 |
| 2005/0010437 | A1 | 1/2005 | Abukwedar |
| 2005/0010449 | A1 | 1/2005 | Abukwedar |

(Continued)

OTHER PUBLICATIONS

American Association of Tissue Banks, Guidance Document, Current Good Tissue Practice, Jun. 27, 2006, pp. 30 and 38.*

(Continued)

*Primary Examiner* — Michael Fuelling
(74) *Attorney, Agent, or Firm* — Moss & Barnett

(57) ABSTRACT

The present invention provides a comprehensive tissue management system for transplantable materials like tissues and organs. The tracking portion of the system prompts and verifies that staff members of a medical establishment like a hospital have handled, stored, transported, reconstituted, and used the tissue or organ materials in a safe and regulatory-compliant manner from the point of receipt to the point of issuance or surgical use throughout the hospital's organization. The tracing portion of the system creates an integral record that documents which hospital staff members have provided which processing steps to the tissue or organ, any associated materials used in conjunction with such tissue or organ, and an identification of the tissue or organ that was transplanted or implanted inside a patient. Such a system will enable adverse reaction investigations for transplant patients, and recalls of transplantable materials.

32 Claims, 16 Drawing Sheets

(56) References Cited

U.S. PATENT DOCUMENTS

| | | |
|---|---|---|
| 2005/0262088 A1 | 11/2005 | Solis et al. |
| 2005/0285715 A1 | 12/2005 | Comunale |
| 2006/0031098 A1 | 2/2006 | Kalthoff et al. |
| 2006/0062771 A1 | 3/2006 | Sasaki et al. |
| 2008/0215363 A1* | 9/2008 | Kasprisin et al. ............... 705/2 |

OTHER PUBLICATIONS

US Dept. of Labor, OSHA Process Safety Management (PSM) standard, reprinted in 2000.*

* cited by examiner

TISSUE MANAGEMENT SYSTEM

CROSS-REFERENCE TO RELATED APPLICATION

This application is a continuation-in-part of U.S. Ser. No. 11/540,844 filed on Sep. 29, 2006 entitled "Comprehensive Tissue Management System," which claims the benefit of the U.S. provisional application No. 60/826,492 entitled "Tissue Tracking and Tracing System" filed on Sep. 21, 2006, both of which are hereby incorporated by reference.

FIELD OF THE INVENTION

This invention relates generally to transplantable materials including cells, tissues and organ transplants ("TM") within the medical field, and more specifically to a computer software-based system for ensuring the safe and appropriate handling of such TM from receipt to their use in surgical procedures and tracing such TM later in response to an adverse reaction investigation or recall.

BACKGROUND OF THE INVENTION

The human body is made up of trillions of cells that allow it to function, grow, heal and defend itself against hundreds of diseases. Cells of the same type combine to form tissues. Examples of tissues include: connective tissue which helps to support and join together various parts of the body; epithelial tissue which acts as a covering for external and internal body surfaces; muscle tissue which consists of threadlike fibers that can contract to make movement of the body possible; and nervous tissue which carries signals to permit various parts of the body to communicate with each other.

An organ consists of multiple tissues working to perform a particular function. For example, connective, epithelial, muscle and nervous tissues all combine to make up the heart which pumps blood throughout the body. The body's skin, skeletal, muscular, digestive, respiratory, circulatory, urinary, lymphatic, endocrine and nervous systems are all formed from multiple organs that in turn are made up of several different kinds of tissues.

When tissues or organs are damaged or diseased, healthy cells, tissues, or organs from one person may be transplanted to replace the diseased, damaged, or destroyed tissue or organ in another person. Blood transfusion is the most common type of tissue transplanted. After blood products the most common transplant from person (allogeneic) is cadaveric tissue: e.g., bone, tendons, skin, cornea, heart valves and blood vessels. There are more than a million tissue transplants a year; most of these are bone and other musculoskeletal tissues. For instance, bone transplants are commonly used in spinal surgery and the transplanted bone attracts new bone formation and eventually becomes an indistinguishable part of the recipient's bone. Cornea transplants improve the vision of the patients whose corneas have become scarred by injury or clouded by age or infection. Skin transplants can be used to temporarily cover areas of the body of burn victims to reduce the risk of infection, prevent the loss of fluids and decrease pain until skin from another part of the patients own body can be utilized for a more permanent transplant. Bone marrow transplants replace the blood-forming tissue within a patient's bones to treat certain kinds of cancer and serious blood disorders.

Tissues are usually isolated and processed for easier use in surgical procedures. For example, whole bones can be used in transplant or bones can be cut into various shapes or powdered to use in filling voids. Bones from different areas of the body can be combined and processed by proprietary methods into new products designed for unique uses in surgical procedures.

Some tissues can be treated more harshly than others and the processing methods will determine the likelihood that a tissue product carries an infectious risk. Tissues such as bone that are treated with alcohol, oxidative agent or irradiation have very low or non-existent risks, but some surgeons are reluctant to use these for fear that the functionality of the product has been compromised. Use of antibiotics does not guarantee that bacteria have been totally removed from the graft and have no effect on viruses.

The heart, lungs, kidney and liver are commonly transplanted organs. Such transplant procedures can enhance the quality of life for some patients and restore the health of people who may otherwise die, Some organs like the heart and lungs cannot survive outside the body for more than a couple of hours. Thus, they usually are transplanted quickly from a patient who has been declared brain dead and surviving only by mechanical means in order to perfuse the organs until they can be transplanted to the matched recipient patient in need. Organ registries have been established in many cities and countries to identify and prioritize transplant patients in need of an organ. Their position on the registry list will typically determine, when, if ever, they can qualify for a transplant. Many tissues like bone, corneas and skin, however, can be held for longer periods outside the human body. Such tissues can be stored for future transplantation or implantation in refrigerators or freezers at independent tissue banks or tissue processors and subsequently distributed to storage units within hospitals.

Infection from contaminated grafts is the greatest risk from transplantation. Tissue and organ transplantations have been associated with risk from HIV, hepatitis, bacterial infections, prior associated diseases such as Creutzfeldt-Jakob Disease (CJD), rabies, fungus infections, West Nile virus, leucocytic choriomeningitis, as well as many others. Any transplant operation carries the risk of rejection by the body's immune system or infection. Surgeons try to prevent rejection by choosing a donor with the same blood type as the recipient patient. Matching HLA antigens between the donor and recipient may also be important for kidney and bone marrow transplants. Immuno-suppressive drugs like azathioprine, prednisone and cyclosporine are also commonly given to the transplant patient to help prevent tissue or organ rejection. Because such immuno-suppressive drugs act to reduce immune activity within the patient, they may also hinder the body's ability to defend itself against infections.

Improper handling of the cells, tissues or organs prior to its use in the transplant operation can adversely impact its functionality once implanted in the patient, or greatly increase the likelihood of an infection or other adverse reaction by the patient. For example, the TM may be stored at the incorrect temperature or outside a sterile environment. The packaging surrounding the TM may become perforated. Prior to surgery, TM may be improperly reconstituted. Blood and tissue banks are typically better than surgical units in hospitals at establishing some procedures for storing cells, tissues and organs; however, once these materials leave their facilities, the safety system can deteriorate rapidly. Hospitals rarely have established policies and procedures for receiving, handling, storing and reconstituting tissues and organs before their use in surgery. Instead, they allow a great deal of individual discretion to the hospital physicians and nurses for these critical activities. Consequently, standards and procedures can differ greatly across the hospital staff to the potential detriment of the patient.

Many hospitals perform no qualification of the donor sources of tissue and organs that they use in surgical procedures. To the extent that the hospitals institute any certification process for their tissue and organ suppliers, the process tends to be directed to issues of price and delivery schedule, instead of whether the supplier is properly registered, licensed, and compliant with prevailing industry safety standards. It is as if tissue and organs are just another form of paper clips that need to be stocked in the hospital's inventory. Suppliers of tissue have even been known on occasion to bring these critical tissues in their car trunks to the hospital operating room without monitoring storage conditions.

While hospital surgical departments may possess refrigeration units for storing tissue and organs, their staffs frequently do not know how to monitor and control the equipment. Moreover, few surgical units possess the necessary training to reconstitute tissue. The blood bank and surgical units within the hospital may possess individual staff members with knowledge but they are outside of each other's control.

All of these problems can lead to adverse reactions, including serious infections, illnesses and even death for the transplant patient. For example, a healthy, 23-year-old Minnesota student underwent a routine, elective knee surgery in 2004 in which cartilage sourced from a cadaver via a reputable tissue bank was used by the surgeon to repair the knee. Unbeknownst to the surgeon, the corpse had sat unrefrigerated for 19 hours, and had been rejected by two other tissue banks. The cartilage also had not been adequately treated to kill bacteria. The student died four days after the surgery from a raging infection.

In another reported case, a California man died in 2006 from the effects of a fungus-infested heart valve that had been recently implanted. Indeed, the United States Food and Drug Administration reports that 207 deaths occur each year from fungus-contaminated heart valves alone.

When such an incident occurs, good medical practice and public health policy requires an immediate investigation of the patient's condition to determine whether the infection, illness or death was caused by the tissue, organ, or surgical procedure, as opposed to an independent condition in the patient. If the surgical procedure was faulty, then the transplant procedure needs to be traced back to the surgeons and nurses involved, the operating room environment, and the equipment involved to reduce the likelihood of a repeat event. If the TM was the cause, then it needs to be traced back to the donor or supplier so that other TM from the same source is immediately removed from inventory and other patients who are transplant recipients of similar TM from the same supplier or donor can be warned and provided appropriate medical care and counseling. Yet, such a tracing process is frequently impossible because many hospitals fail to log in the TM that they receive from suppliers and track their use in surgical procedures. Quality problems in hospitals culminated in 2005 when there was a major recall of tissue products inappropriately released by several tissue banks. Yet, repeated attempts to locate tissue products at hospitals that had not been transplanted failed miserably, thereby resulting in other patients receiving potentially contaminated tissue products. During the same recall, hospital protocols for tracing recipients of the potentially contaminated products were found to be substantially inadequate or entirely absent. Close to one year later, there are recipients yet to be identified who have not received appropriate diagnostic treatments and modalities.

Likewise, most hospitals do not have good systems implemented for gauging compatibility between donors and recipients for organs. In one incident reported within the industry, organs provided by a donor institution resulted in several cases of hepatitis C in the transplanted patients. Because the hospital failed to notify the tissue bank for 16 months, other infected patients were deprived of treatment while this disease could be treated, resulting in additional deaths. A $32 million damage award resulted from a subsequently filed litigation.

In addition, there have been reported cases of physicians taking diseased tissue from in-hospital patients and transplanting it into unsuspecting, healthy patients. These tissues have not been able to be tracked back to the original source, resulting in the recipient's death.

The transplant industry relies upon "tissue usage information cards" that a hospital is supposed to return to the issuing tissue bank after a surgical procedure is completed. Such cards allow the tissue bank to monitor usage of their tissue and notify everyone who has received similar tissue for recall purposes. However, hospitals only return 50-85% of these cards to the tissue banks.

In the case of adverse reaction investigations, hospitals do not usually define what constitutes an adverse reaction and therefore what should be reported. Instead, the reporting responsibility is left to the physician's discretion. Physicians often resort to a gram stain test or cultures on the tissue prior to surgery. But, such test results can be misleading and grossly inadequate to detect diseased tissues.

There are associated risks with tissue transplantation. There are numerous reports of transplant-transmitted infections, including some that resulted in death. For example, there was a recent article (Morbidity and Mortality Weekly Report 2002 ("MMWR"); 51 (March 15): 207-210) that reported that on Nov. 7, 2001, a 23-year-old male from St. Cloud, Minn. had knee surgery using a refrigerated "fresh" femoral condyle. On Nov. 10, 2001, the patient developed knee pain and severe hypotension. On Nov. 11, 2001, the patient died from clostridium sordelli sepsis that came from the tissue transplant. On Nov. 13, 2002, a 17-year-old male in Illinois also received a "fresh" femoral condyle and meniscus from the same donor. On Nov. 14, 2002, the patient developed a fever and septic arthritis. The presumed cause was a clostridia infection. Likewise, usage of antibiotics in patients prior to surgery can mask problems contained in tissues.

Because of these abuses and other safety problems within hospital and tissue bank environments, regulatory and standard setting agents like the Joint Commission for the Accreditation of Health Care Organization ("JCAHO"), American Association of Blood Banking ("AABB"), Food & Drug Administration ("FDA"), and the College of American Pathologists ("CAP") are currently implementing mandates for the safe handling, storage, use, and tracing of TM. However, these mandates provide no instructions or guidelines to the hospital or tissue bank for how to comply. Therefore, such hospitals and tissue banks are left with regulatory and legal liability for their failure to comply, but no tools to use to comply.

Some instances of tissue tracking are reported in the prior art. Thus, U.S. Published Application No. 2005/0262088 filed by Solis et al. discloses a system for organ procurement and transfer. While this system maintains the security of patient information, it does not address the safety of the organ or organ match for the patient.

U.S. Published Application Nos. 2005/0010437 and 2005/0010449 filed by Abukwedar teaches an organ donation system that permits a person to donate or agree to donate one type of organ in order to be accorded preferential receipt of another organ. This exchange program, however, does nothing for tracking the safe receipt, handling, or use of the organ, or tracing its use after surgery.

U.S. Published Application No. 2005/0285715 filed by Comunale discloses a container with an electronic lock controlled by a computer system for carrying blood samples or organs to a hospital in a secure manner. While this transportation container can prevent theft or contamination of the organ by strangers, it does nothing to prevent unsafe handling, storage, or treatment by the hospital of the organ.

Other prior art systems exist within a diagnostic laboratory, for tracking biological samples. Thus, U.S. Published Application No. 2003/0120633 filed by Torre-Bueno assigns unique bar codes to samples that can be scanned and read during processing of the sample within the lab. U.S. Pat. No. 5,416,029 issued to Miller et al. employs color-coded embedding media and corresponding color-coded slides accompanied by words, numbers, or symbols to identify the biological samples. U.S. Pat. No. 5,842,179 issued to Beavers et al. discloses a cryogenic freezer with a security key pad for receiving and tracking information to identify the location of blood and tissue samples stored within the freezer, and when a capsule has been removed from the freezer. While these types of systems may be useful for keeping track of thousands of biological samples stored within a diagnostic laboratory, they do nothing to ensure the safe handling, storage, and treatment of the sample within the lab.

Other prior art references disclose systems for keeping track of the whereabouts of surgical supplies used during surgery to detect if they have been accidentally left inside the patient after surgery. See, e.g., U.S. Published Application No. 2002/0049650 filed by Reff, and U.S. Pat. No. 6,861,954 issued to Levin. U.S. Published Application No. 2002/0082957 filed by Krassi specifies an inventory control system for chemical reagents used within a clinical or diagnostic lab. Such inventory control tracking systems can detect the location or number of products, but once again, they do not address the proper handling and storage of those products.

A comprehensive system for tracking the appropriate handling, storage and use of tissues and organs throughout the tissue bank's or hospital's chain of custody of the materials would be beneficial. Also advantageous would be a system that reliably enables the tracing back of tissues or organs from patient to supplier after an adverse reaction is detected. For tissue and blood banks and larger healthcare providers, this system would ideally be computerized due to the comparatively large number of TM that need to be processed and handled.

Indeed, computer systems are used within the healthcare industry to store, monitor, and track patient information. The hard drives of such computer systems can store large volumes of data which can be password-protected. National home health agencies, hospitals and medical clinics can afford to employ large computer systems run on "point of care" software that permit the clinician to call upon a file containing the medical chart for a patient from the computer's hard drive, review the patient's initial physical assessment, clinical procedures and medicines administered in the past, and update the file for any new clinical procedures or medicines prescribed. Such computer software systems provided by companies like 3M Corporation, Care Package, and St. Louis Software are readily accessible by different doctors or nurses at the hospital or clinic. However, such point-of-care software systems are necessarily complex because of the large number of patients and clinical staff required to access the information It is not uncommon for such programs to require expensive database platform servers and cost upwards of $100,000.

Other computer software systems are known within the industry for assisting the administration of medical care. For instance, U.S. Application 2004/0186746 by Angst on Sep. 23, 2004 discloses a USB flash memory device that permits a user to carry his personal medical records with him and launch it on the hard drive of any computer. The information contained within the flash memory device can be protected via a password or encryption. In this manner, the user has accurate medical records for himself when he visits the doctor, or in case of a medical emergency.

Computerized information devices can also be used to monitor a patient in the field. U.S. Application 2004/0117207 published by Brown on Jun. 17, 2004 teaches a handheld microprocessor device used by a patient to monitor and store, e.g., blood glucose level data. This information can then be transmitted to a doctor at a remote location and downloaded by the doctor onto a computer for storage or to produce medical reports.

Many patients do not actually visit a hospital, medical clinic, or doctor's office for medical care due, e.g., to a loss of mobility or frequency of required care. Thus, the doctor or nurse may visit the patient at her home. In such cases, the medical practitioner is away from his office where the medical records, medical treatises and studies, etc. reside. Therefore, U.S. Patent Application 2004/0249666 published by Napolitano et al. provides a healthcare computerized system that provides medical practitioners with best practice patient disease diagnosis and treatment information. In essence, it enables the medical practitioner to carry a bookcase of medical treatises and published studies with her. The practitioner can use this portable information to diagnose and treat the patient in the field.

U.S. Patent Application 2005/0027567 published by Taha on Feb. 3, 2005 on the other hand discloses a data management system containing a field module used by the medical practitioner to collect data for the patient and communicate it back to a server at the home office for use by a doctor or nurse to tell the field practitioner what steps to take to treat the patient. The patient can also use this field module to communicate with his caregiver back at the medical office. See also U.S. Application 2002/0194029 published by Guan et al. on Dec. 19, 2002 which discloses medical information management system that permits a medical practitioner to carry a patient's medical records with him in image form in the field, consult medical on-line databases, and communicate remotely with other members of the medical staff.

Computer systems are also widely used for dispensing medicines in hospitals via, e.g., an infusion pump. See U.S. Application 2005/0065817 published by Mihai et al. on Mar. 24, 2005; 2005/0055244 published by Mullan et al. on Mar. 10, 2005; and 2005/0055242 published by Bello et al. on Mar. 10, 2005. Such systems typically track and monitor the patient's symptoms to indicate how the administered drug is affecting the patient.

These information management systems available within the healthcare industry typically focus upon "point of care" for the patient, keeping track of all the clinical data for treatment of that patient. At least one computer system is also available from Owens & Minor within the healthcare industry for tracking TM. However, this system provides essentially the same functionality as conventional paper records systems. It does not permit queries directed to TM data, does not track the healthcare institution's processing and handling of the TM, and provides no mechanism for prompting or enabling the healthcare institution to investigate an adverse reaction occurring in the patient. Likewise, large national blood banks use computerized systems to track their massive inventories of blood samples. Such systems keep track of the blood type of each sample, so that a blood sample is not supplied to a patient with an incompatible blood type. Such systems will also provide advice regarding which blood type are compatible and which ones are not from a safety stand point. However, these blood bank computerized systems represent little more than inventory systems without any functionality for tracking the processing and handling of the blood samples.

Thus, a comprehensive computerized system that permits the tracking of the appropriate handling, processing, storage, and use of tissues and organs throughout the tissue bank's or hospital's chain of custody of the materials would be beneficial, particularly if its built-in functionality prompts staff members of the tissue bank or hospital to record necessary data and properly handle, process, store, and use the tissue or organ product. Such a computerized system would also be advantageous if it provides a search or query functionality that reliably enables the tracing back of tissues or organs from patient to supplier after an adverse reaction is detected, or the tracing forward of the material from supplier to patient or hospital in the event of a product recall.

SUMMARY OF THE INVENTION

The present invention provides a comprehensive tissue management system for transplant materials like tissues and organs. The tracking portion of the system verifies that staff members of a medical establishment like a hospital have handled, stored, transported, reconstituted, and used the tissue or organ materials in a safe and regulatory-compliant manner from the point of receipt to the point of issuance or surgical use throughout the hospital's organization. Such a system is preferably computer-based, and it should preferably be structured to provide appropriate prompts to the staff members to take the necessary actions to handle, store, transport, reconstitute and use the tissue or organ materials in a safe or appropriate manner. Even more preferably, such system will not permit such staff members to carry out a step for handling, storing, transporting, reconstituting or using such tissue or organ material unless data has already been entered into the system to verify that a prior necessary step has been taken.

The tracing portion of the system creates an integral record that documents which hospital staff members have provided which processing steps to the tissue or organ, any associated materials used in conjunction with such tissue or organ, and an identification of the tissue or organ that was transplanted or implanted inside a patient, so that the tissue or organ can be reliably traced back to its donor or tissue bank source in the event of an adverse reaction by the patient after the surgery, or the tissue or organ can be traced in response to a warning received from the donor or tissue bank. Such adverse reaction investigation is preferably conducted utilizing medical cladistics to identify risk clades. Again, such system, preferably computer-based, should be structured to provide prompts to the medical establishment's staff members to record and enter the data at the same time that the processing activity is carried out in order to create accurate, comprehensive and contemporaneous record-keeping. Such system preferably will refuse to permit the staff members to enter data into the system for a processing step unless data from a previous processing step has already been entered.

BRIEF DESCRIPTION OF THE DRAWINGS

In the accompanying drawings:

FIG. 6 is an interactive graphic user interface illustrating a vendor information subscreen.

FIG. 7 is an interactive graphic user interface illustrating a tissue order screen.

FIG. 8 is an interactive graphic user interface illustrating a tissue receipt screen.

FIG. 11 is an interactive graphic user interface illustrating a tissue management screen.

FIG. 12 is an interactive graphic user interface illustrating a change tissue location subscreen.

FIG. 13 is an interactive graphic user interface illustrating a tissue storage history subscreen.

FIG. 16 is an interactive graphic user interface illustrating a tissue usage information card screen.

FIG. 17 is an interactive graphic user interface illustrating an adverse reaction reporting screen.

DETAILED DESCRIPTION OF THE PREFERRED EMBODIMENT

Figure 1:
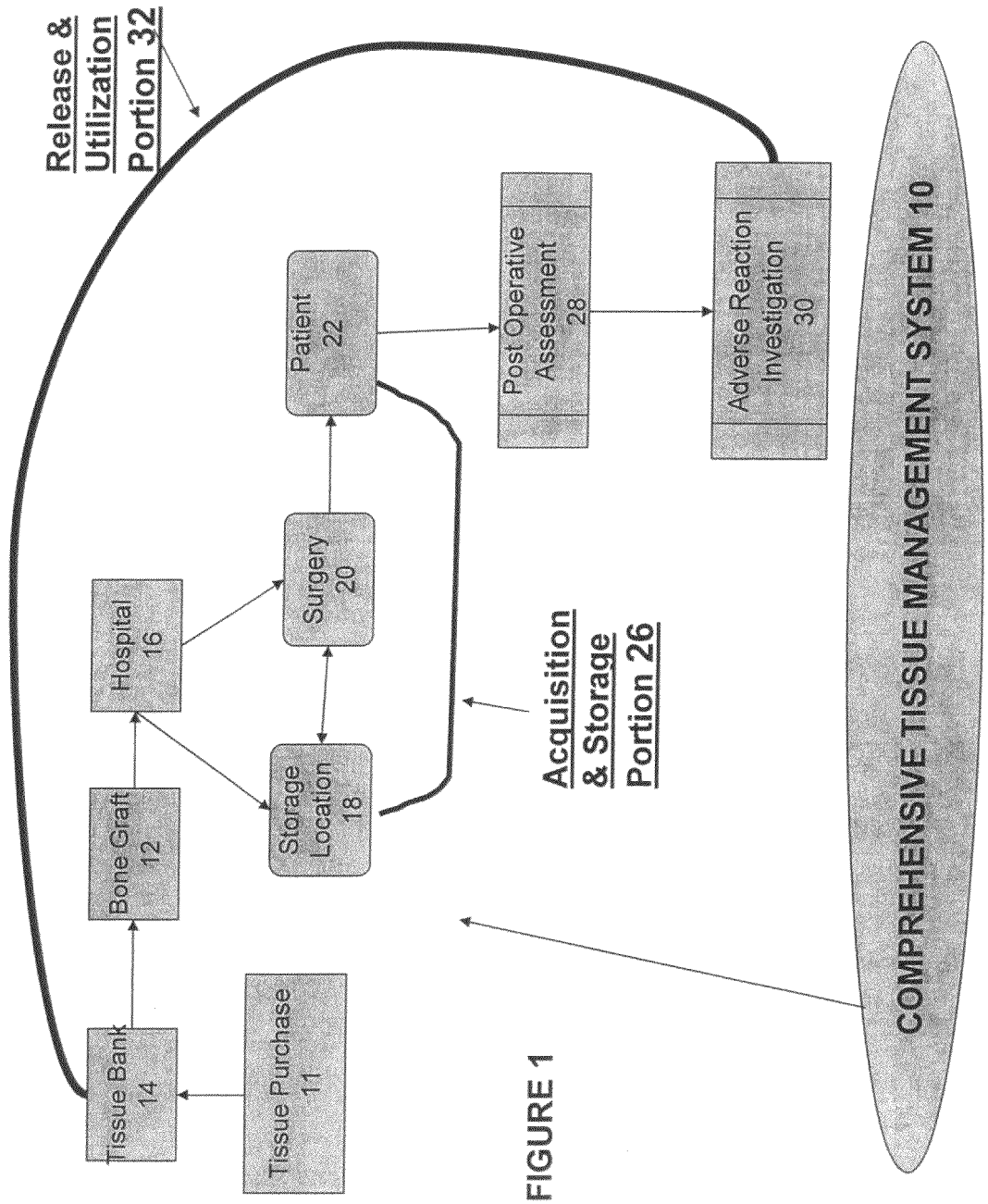
FIG. 1 is a schematic illustration of a process flow for the transfer and use of transplantable material within a clinical environment.

A comprehensive system for safe management of transplantable material is provided by the invention. In its preferred embodiment, the system is computer-based. Such invention enables the proper qualifications of vendors, logging and inspection of incoming transplantable material, product maintenance, integrated tracking and verification of the handling, storage, and use of transplant materials in a safe and regulatory-compliant manner from the point of receipt to the point of issuance/final disposition throughout the medical establishment. The system also provides for prompt investigation of any adverse reaction suffered by a patient who receives the transplantable material through a surgical procedure. Additionally, it ensures a complete documented history of the transplantable material within the medical establishment so that the transplantable material can be traced back to its supplier in the event that a product recall of transplantable material is warranted, or a supplier issues such a recall notice. This allows a timely identification, notification and treatment of other patients receiving similar transplants.

The system of this invention is tailored to the specific medical establishment and its handling and use of transplant materials, so as to enhance the integrity of the system. Moreover, the system prompts staff members of the medical establishment to carry out the necessary steps for the safe and appropriate processing of the transplantable material and to record the associated data at the time that the activity is conducted. More preferably, the system will not allow data entry for a processing step unless the data from a prior processing step has already been entered and the pre-qualified staff has entered the information. In this manner, the system provides a self-auditing function to enhance the integrity of its tracking and tracing functionalities.

For purposes of the present invention, "transplantable material ("TM")" means human cells, tissue, or organs intended for implantation, transplantation, infusion, or transfer to a patient, including, but not limited to: musculoskeletal tissues like bone, tendons, fascia, ligaments, cartilage, and bioengineered bone products; skin; cardiovascular tissues like heart valves, arteries, veins, and pericardium; reproductive cells like sperm, semen, oocytes, fertilized eggs, and embryos; cellular therapies like stem cells, progenitor cells, cord blood, placental blood, chondrocytes, bone marrow, and neural cells; dura mater; breast milk; eyes; corneas; organs; islet cells; parathyroids; autologous tissue; and synthetic and xenographic tissue used as replacements for human tissue. For purposes of this application, transplantable material also includes surgical instruments, equipment, reagents, supplies, and other materials associated with the transplanting or implanting of any transplant material into a patient.

In the context of the present invention, "medical establishment" means any organization directed to the storage, research, transplantation, or implantation of transplantable materials, including but not limited to hospitals, medical clinics, surgical centers, fertility clinics, blood banks, tissue banks, organ donor banks, university and research facilities, diagnostic laboratories, and willed body programs.

As used within this application, "supplier" means any person or entity that provides a transplantable material to a medical establishment on a profit or non-profit basis, including but not limited to live or deceased organ donors, tissue banks, blood banks, fertility clinics, laboratories, and manufacturers of synthetic or bioengineered tissue or organ products.

For purposes of the present invention, "patient" means any recipient by transplantation or implantation of a transplantable material, including without limitation humans, domesticated animals like dogs, cats, and horses, and working animals like bulls and stallions.

As used within this application, "adverse reaction" means any undesirable effect or untoward outcome consequent to or reasonably related to the transplantation or implantation of transplantable material into a patient, including but not limited to disease transmission, other infectious complications like fever or wound infection attributed to the graft or positive culture of the graft at the time of use, immune rejection, and unexplained synovitis following tendon implant.

A freeze-dried bone graft implanted into a human patient will be used as an exemplary transplant material for purposes of describing the comprehensive tissue management system of the present invention in this application. It is important to appreciate that any other type of transplantable material (tissues, cells or organs) or patient is covered by this application, as well.

FIG. 1 shows the history of a tissue transplant from entrance into the hospital to the final implantation in a patient. When a surgeon is in need of a bone graft 12, the hospital 16 will acquire it from a tissue bank 14 by placing a purchase order 11. The bone graft 12 will be acquired by hospital 16 in accordance with the terms of its supply agreement with the tissue bank 14. Once the bone graft 12 is delivered to hospital 16 by tissue bank 14, it will typically be stored by the hospital. The location of storage 18 varies by hospital. It can include the blood bank, surgical department, central supply, etc. until the bone graft is needed by the hospital's surgical department 20 for implantation into patient 22. The comprehensive tissue management tracking portion 26 of the present system prompts the hospital staff to undertake all of the activities necessary for the safe handling, storage, reconstitution, and implantation of the bone graft 12 in accordance with regulatory requirements and industry standards from the point of receipt by the hospital 16 until the bone graft is implanted into patient 22, and collects the necessary information to document the staff's compliance therewith.

Once the bone graft 12 has been implanted into the patient 22, the medical establishment's responsibility to the patient is not complete. Instead, the surgeon or other staff member of the hospital 16 needs to perform a post-operative assessment 28 of the patient's condition to determine whether any adverse effect like infection caused by the bone graft or surgical procedure has occurred. The hospital then notifies the tissue bank by usage of the tissue utilization information card ("TUIC") to whom the tissue was implanted. If an adverse reaction occurs, then an investigation 30 needs to be promptly commenced to determine whether the adverse reaction was caused by the bone graft, the surgical procedure, the reagents used to reconstitute the bone graft or some independent condition of the patient 22. The comprehensive tissue management tracing portion 32 of the present system enables the reliable tracing of the bone graft back to the tissue bank 14 in the event of an adverse reaction investigation 30, or the tracing forward of the bone graft 12 to the patient 22 or the storage inventory location 18 in the event that tissue bank 14 issues a recall or other warning.

The comprehensive tissue management system portions 26 and 32 of the present invention must have compiled a sufficient documentary history of the bone graft throughout its life in the hospital to enable the investigation to identify each aspect of the handling, storage, reconstitution, and surgical implantation of the bone graft 12 back to tissue bank 14 as the supplier in the event that a recall of other transplantable material from the same donor is necessary. Identification of other patients receiving such similar tissue products must be conducted. This is followed by notification to the patients and determination of possible medical treatment.

Figure 2:
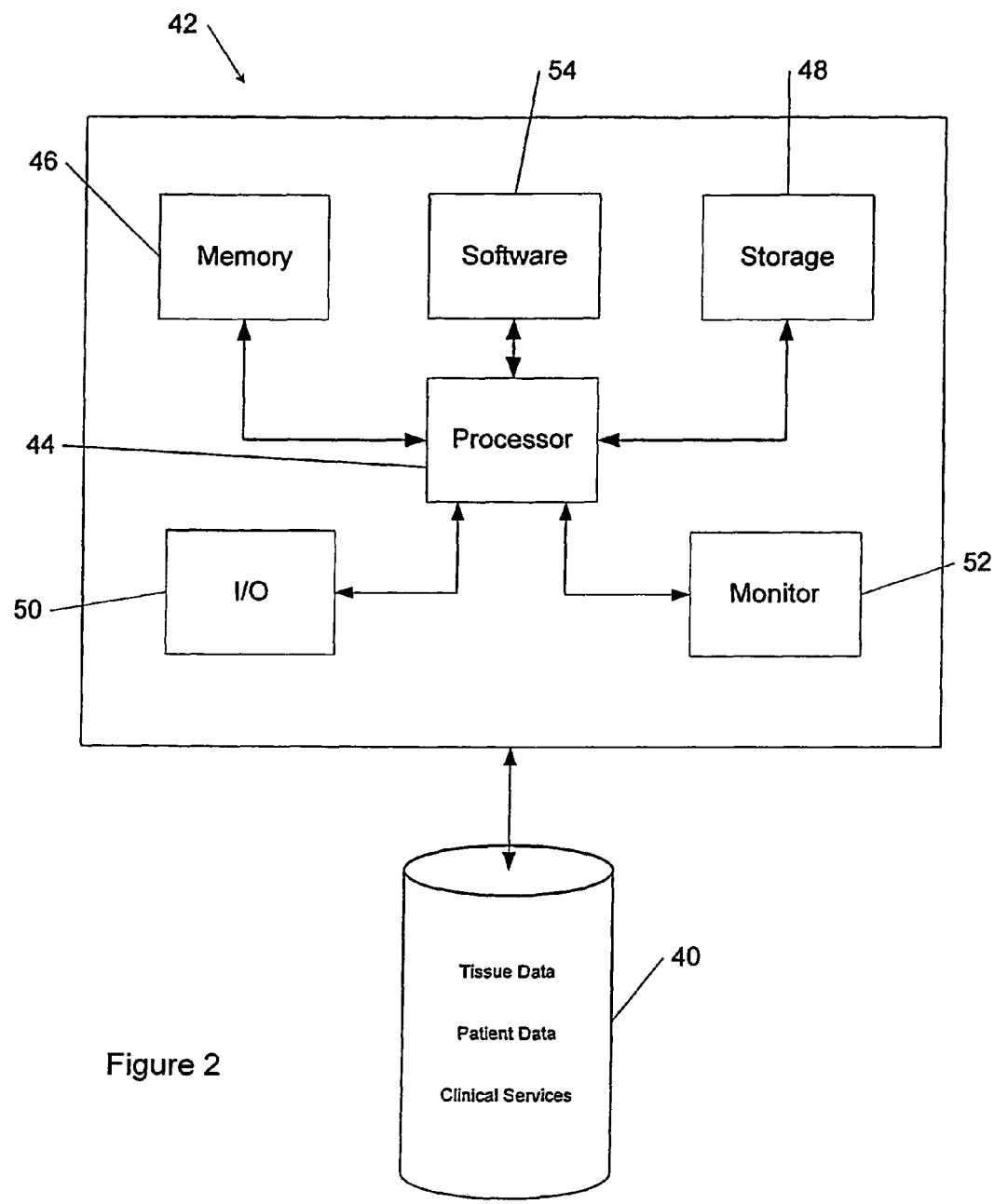
FIG. 2 is a flow diagram illustrating an example embodiment of a system for managing a comprehensive tissue management method and recording information related thereto.

Referring to the example embodiment of FIG. 2, the comprehensive tissue management system 10 comprises a general programmable computer 42 having a central processing unit ("CPU") 44 controlling a memory unit 46, a storage unit 48, an input/output ("I/O") control unit 50, and at least one monitor 52. Computer 42 operatively connects to database 40, containing, e.g., tissue data, patient data, and clinical services data. It may also include clock circuitry, a data interface, a network controller, and an internal bus. One skilled in the art will recognize that other peripheral components such as printers, drives, keyboards, mousse and the like can also be used in conjunction with the programmable computer 42. Additionally, one skilled in the art will recognize that the programmable computer 42 can utilize known hardware, software, and the like configurations of varying computer components to optimize the storage and manipulation of the data and other information contained within the comprehensive tissue management system 10.

The software program 54 may be designed to be an expression of an organized set of instructions in a coded language. These instructions are programmed to facilitate the monitoring of the transplantable material from at least the point of sourcing, handling, transportation, storage, reconstitution and/or surgical implantation. The instructions may include the entry, reporting and/or reading of data relating to time, date, location, temperature, condition of the tissue, and/or any other information needed for monitoring the transplantable material.

The computer system on which the system resides may be a standard PC, laptop, mainframe, handheld wireless device, or any automated data processing equipment capable of running software for monitoring the progress of the transplantable material. The CPU controls the computer system and is capable of running the system stored in memory. The memory may include, for example, internal memory such RAM and/or ROM, external memory such as CD-ROMs, DVDs, flash drives, or any currently existing or future data storage means. The clock circuit may include any type of circuitry capable of generating information indicating the present time and/or date. The clock circuitry may also be capable of being programmed to count down a predetermined or set amount of time. This may be particularly important if a particular type of tissue needs to be refrigerated or implanted in a predetermined amount of time.

The data interface allows for communication between one or more networks which may be a LAN (local area network), WAN (wide area network), or any type of network that links each party handling the tissue. Different computer systems such as, for example, a laptop and a wireless device typically use different protocols (i.e., different languages). To allow the disparate devices to communicate, the data interface may include or interact with a data conversion program or device to exchange the data. The data interface may also allow disparate devices to communicate through a Public Switched Telephone Network (PSTN), the Internet, and private or semi-private networks. Referring to FIG. 2, comprehensive tissue management system 10 includes a software program 54 having a plurality of graphic user interfaces ("GUIs") are displayed to a user in a text or graphical form to permit the input of data concerning the patient 22, the purchase order 11 placed for the bone graft 12, and the receipt, storage, handling, transport, reconstitution, and surgical use of the bone graft with respect to patient 22. The GUI can also be used to display the status of the transplantable material to any or selected staff members participating in monitoring the transplantable material. Additionally, the comprehensive tissue management system, computer system, and GUI can be connected to external devices such as refrigeration units to send a current temperature reading or to notify those monitoring the tissue that the temperature of the refrigeration unit has decreased or increased beyond a predetermined range. The comprehensive tissue management system, computer system, and GUI can be connected to any type of device that needs to be monitored.

Data may also be inputted with respect to the post-operative assessment 28 of the transplant or implant, and any adverse reaction investigation 30 resulting therefrom. Outputs produced by such software program 54 include search results directed to the bone graft 12, its current location in storage location 18 or the patient 22 into which it was transplanted or implanted, and all processing steps carried out with respect to the bone graft and which staff members conducted those processing steps. The software program 54 can also produce and print a series of reports documenting this information.

Figure 3:
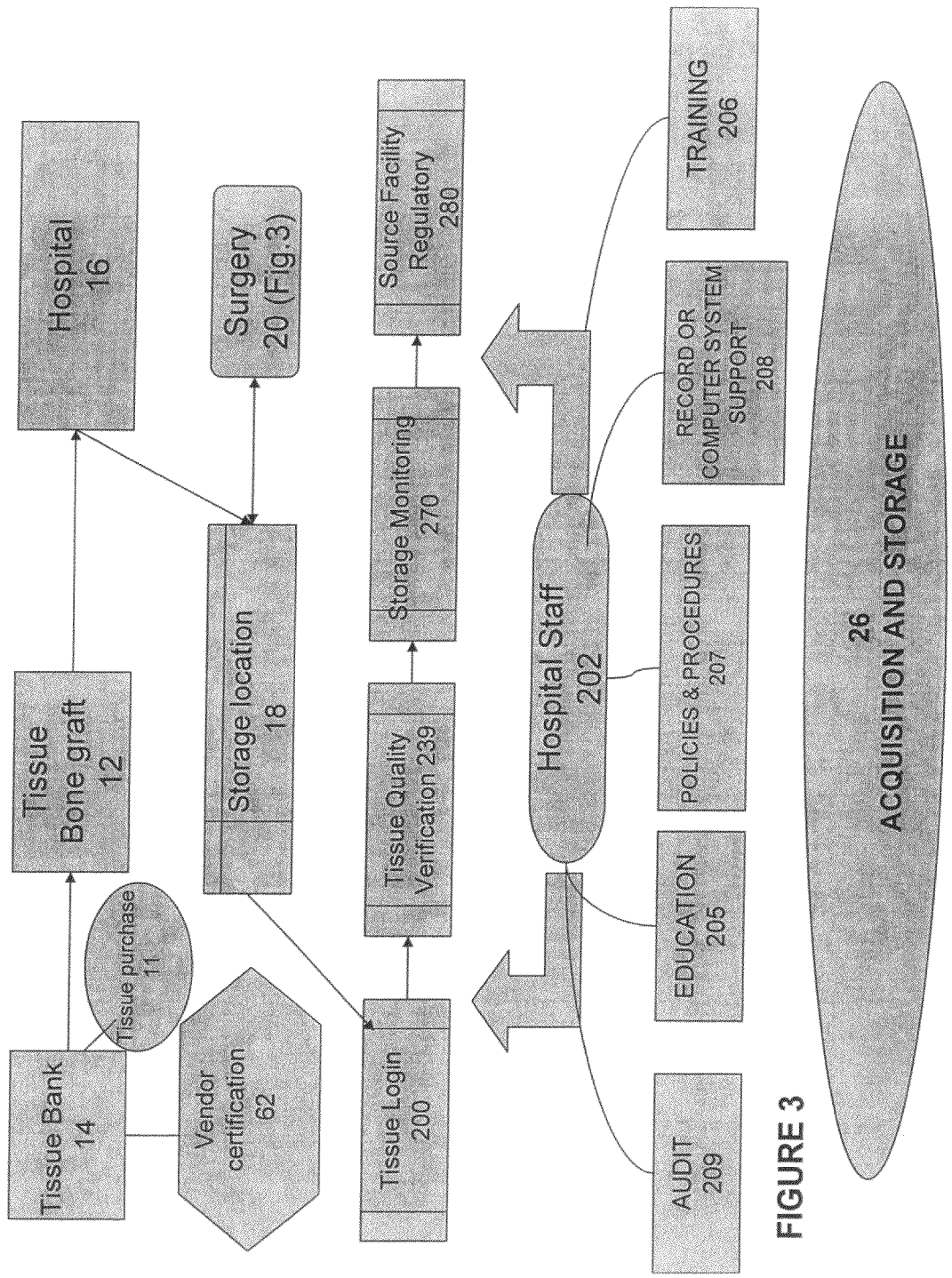
FIG. 3 is a schematic diagram showing the storage and acquisition portion of a comprehensive tissue management system.

The acquisition and storage portion 26 of the comprehensive tissue management system 10 is shown in detail in FIG. 3. The first aspect of the system is supplier certification 62 of the tissue bank 14. The present invention prompts the medical establishment to create criteria to determine the guidelines for selecting a vendor.

Rather than merely rely upon the name and reputation for quality and safety of the supplier as many hospitals do, this process step of the system requires affirmative verification that the tissue bank complies with all of the regulatory requirements and industry standards applicable to the sourcing, storage, and handling of transplant materials. At the most basic level, this can consist of documenting that the tissue bank 14 is currently registered with the FDA to supply that kind of tissue—in this case bone graft 12. Such FDA registration documentation may be obtained directly from the tissue bank 14, or from the FDA, including the FDA's Website: https://www.accessdata.fda.gov/scripts/cber/CFAppsPub/tiss/index.cfm.

Some states like New York, California, Georgia, Maryland and Florida require that tissue source facilities (processors, tissue banks, and distributors) be specially licensed for this purpose. Again, documentation of this state license may be obtained directly from tissue bank 14, or else from the applicable state licensing agency. One must ensure that the FDA registration and applicable state licensure pertain to each type of transplant material to be sourced from tissue bank 14. Supplier certification step 62 more preferably may include directly auditing the tissue bank concerning their policies and procedures for sourcing, storing, handling, and transporting the transplant materials, and personally inspecting their facilities. Much relevant information can be obtained from such direct efforts to certify the performance of the tissue bank 14.

This supplier certification step 62 can also preferably be supported by the hospital 16 entering into a memorandum of understanding or other contract with the tissue bank to comply with all regulatory requirements and industry standards for safely sourcing, storing, handling and transporting the transplant materials. The tissue bank may take its responsibilities more seriously if it risks contractual breach and damages in addition to potential loss of its FDA registration and state license.

Figure 4:
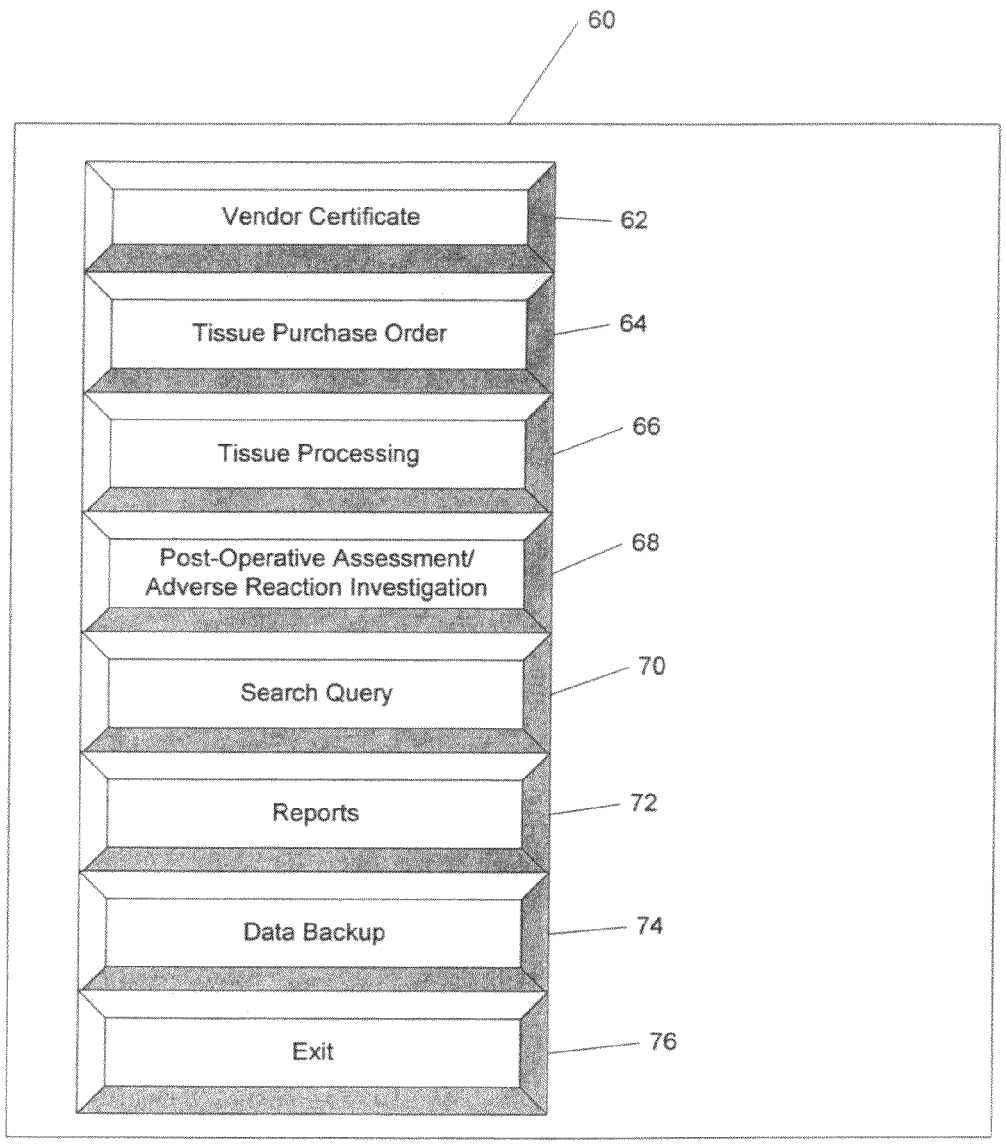
FIG. 4 is an interactive graphic user interface illustrating a main menu of functions for the comprehensive tissue management system.

The home screen GUI 60 of the software program 54 is shown in FIG. 4. By marking or checking a box or similar marking indicator, a user can enter certification information for suppliers 62; place a purchase order 64 to a supplier such as tissue bank 14 for transplantable material like tissue bone graft 12; enter processing data 66 relating to the login, quality verification, storage, handling, transportation, reconstitution, and surgical use of the bone graft 12; enter data 68 relating to the post-operative assessment of the patient and any adverse reaction investigation resulting therefrom; perform a search 70 based upon any of this data; generate a report 72 incorporating some of the data; or back up the data 74 contained within the comprehensive tissue management system 10. Icon 76 provides a simple and direct means for exiting the software program 54 for the comprehensive tissue management system 10.

Figure 5:
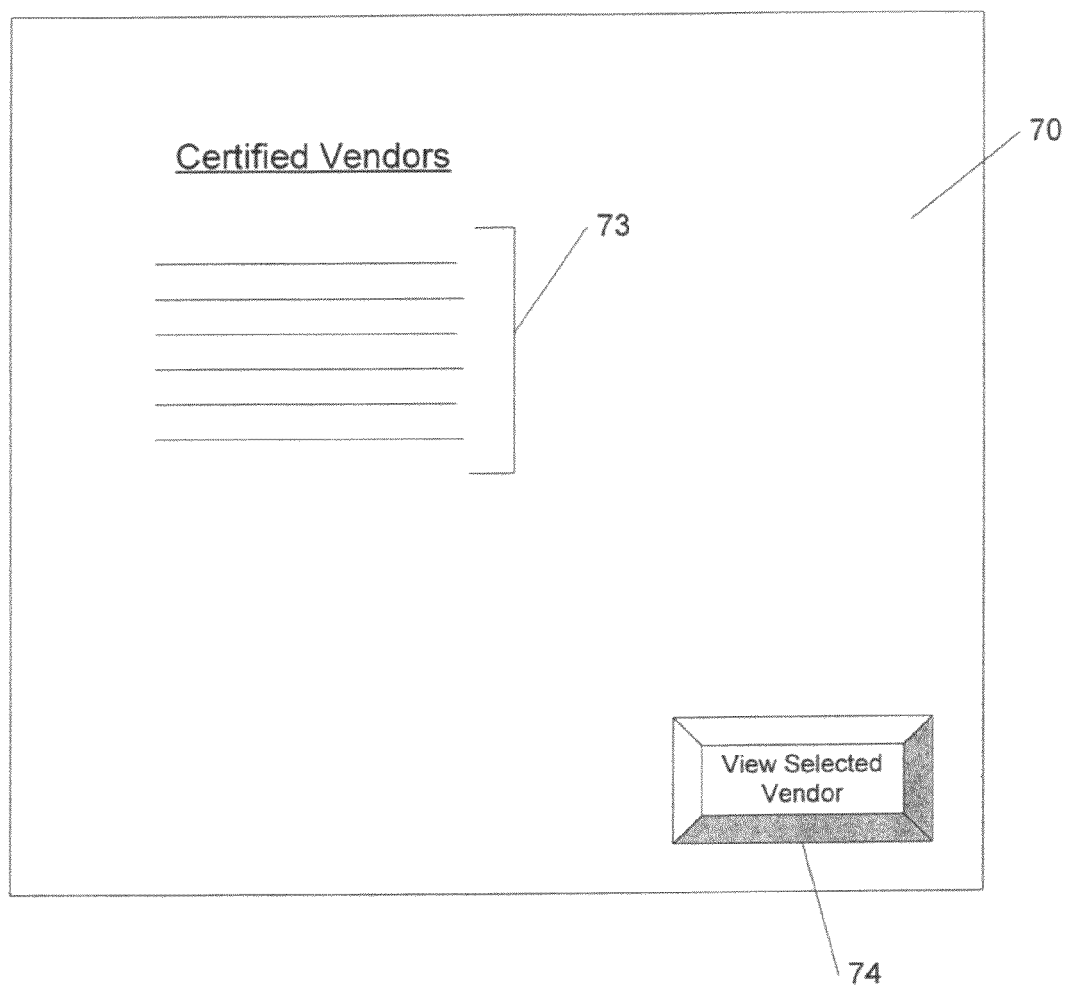
FIG. 5 is an interactive graphic user interface illustrating a certified vendors list screen.
Figure 6:
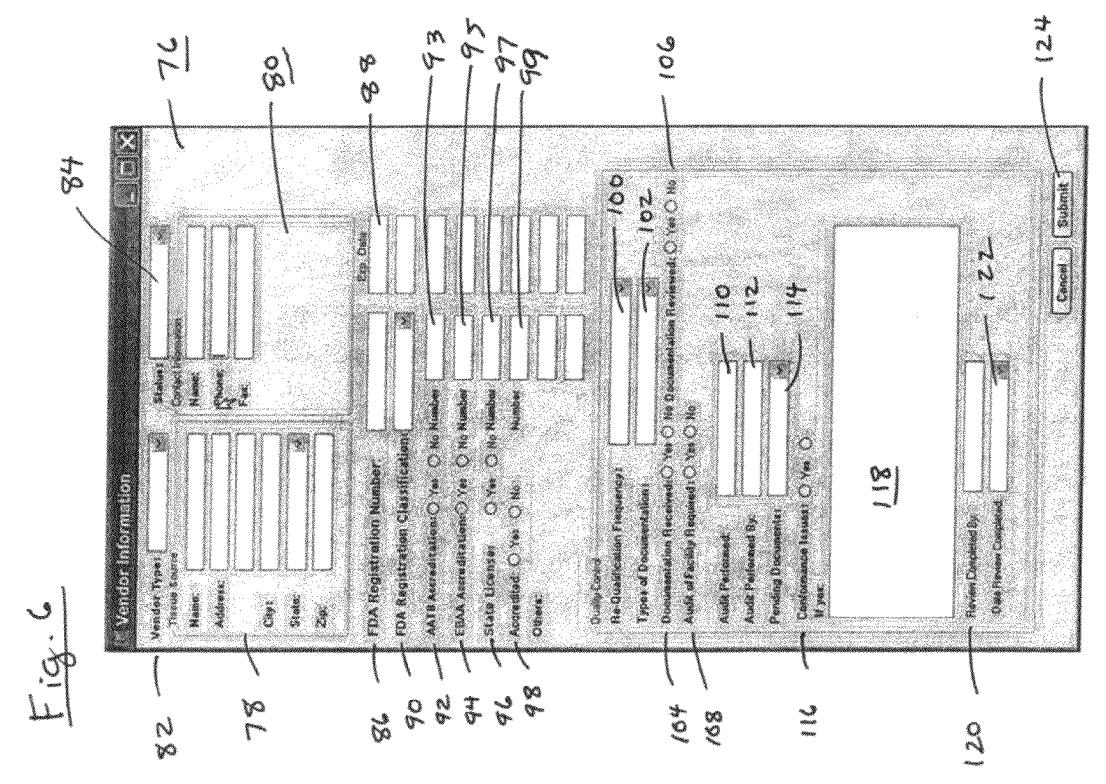

By clicking on icon 62 of the home screen GUI, the user calls up the certified vendors GUI 71 shown in FIG. 5. This list contains all of the certified tissue suppliers that have been entered into the software program. By double clicking on one of the vendor entries 73, or highlighting a name and then clicking on the "view selected vendor" icon 74, the vendor information GUI 76 for a specific vendor is called up, as shown in FIG. 6. This is the principal GUI screen contained within the comprehensive tissue management system 10 for providing background information concerning the vendor.

As shown in FIG. 6, field 78 permits the name, street address, city, state and zip code for the vendor ("tissue source") to be recorded. A specific contact name, phone number, and fax number may also be entered within field 80. A drop down box within field 82 contains identifying types for the vendor, such as "tissue bank", "distributor", "blood bank", or a hospital name that supplies the transplantable material. Field 84 provides another drop down box containing options for identifying the status of the vendor—e.g., approved, unapproved, or pending.

Very importantly for purposes of the comprehensive tissue management system 10 of the present invention, the user is prompted within field 86 to enter the FDA Registration Number for the vendor, as well as the expiration date 88 for that FDA registration. The FDA registration classification must also be selected from the drop down box in field 90. This information represents proof that the specific vendor is in good standing by the FDA to supply transplantable materials. More preferably, the comprehensive tissue management system 10 could require this FDA registration information to be entered and confirmed for a particular type of transplantable material, since a vendor will usually not be certified by the FDA to supply all types of transplantable materials.

The Vendor Information GUI 76 shown in FIG. 6 also prompts the user to select the appropriate "yes/no" choices for AATB accreditation 92, EBAA accreditation 94, state licensure 96, and other accreditation as required by the hospital 98 for the vendor. In the case of a "yes" answer, the specific number 99 is entered for the AATB accreditation 93, EBAA accreditation 95, state license 97, or accreditation 98.

For purposes of quality control, the vendor information GUI 76 shown in FIG. 6 also prompts the user to identify from a drop down box in field 100 the frequency with which the registration and accreditation credentials of the vendor should be reconfirmed, as well as the type of documentation 102 that should be checked. This information is important, since a vendor may lose its FDA registration or state license status to supply a type of transplantable material, and the medical establishment will want to know this fact before it orders transplantable materials of that type from that vendor. The frequency of this registration or accreditation reconfirmation will be a time period that corresponds to the risk profile that is acceptable to the medical establishment, such as six months, one year, or two years. Fields 104 and 106 of the vendor information GUI 76 also prompt the user to confirm whether or not documentation used to reconfirm the registration/accreditation credentials for the vendor have been received and reviewed.

Finally, a medical establishment may choose to audit the vendor on a periodic basis in order to provide additional information for confirming that the vendor is a safe source for providing transplantable materials of a particular type. The medical establishment's internal requirement that the vendor facility be audited should be noted in field 108. Once an audit is actually performed upon the vendor facility, the performance date, individual performing the audit, and pending documents should be recorded in fields 110, 112 and 114, respectively. The existence of any conformance issues resulting from the audit is noted in field 116, and further defined within the information box provided by field 118. The individual who performed the review of the audit documentation and defined the conformance issues should be entered within field 120, along with the review date recorded within field 122. Once all of this information is entered into GUI 76, the "submit" button 124 should be selected in order to enable the comprehensive tissue management system 10 to process the information and populate screens within other associated GUI's of the system.

Transplantable materials like the tissue bone graft 12 may be ordered in step 11 of the acquisition and storage portion 26 shown in FIG. 3 of the comprehensive tissue management system 10 of the present invention. By clicking on the "tissue purchase order" icon 64 of the home GUI 60 depicted in FIG. 4, tissue order 132 shown in FIG. 7 will be called up to enable placement of a purchase order with a vendor for the bone graft.

Figure 7:
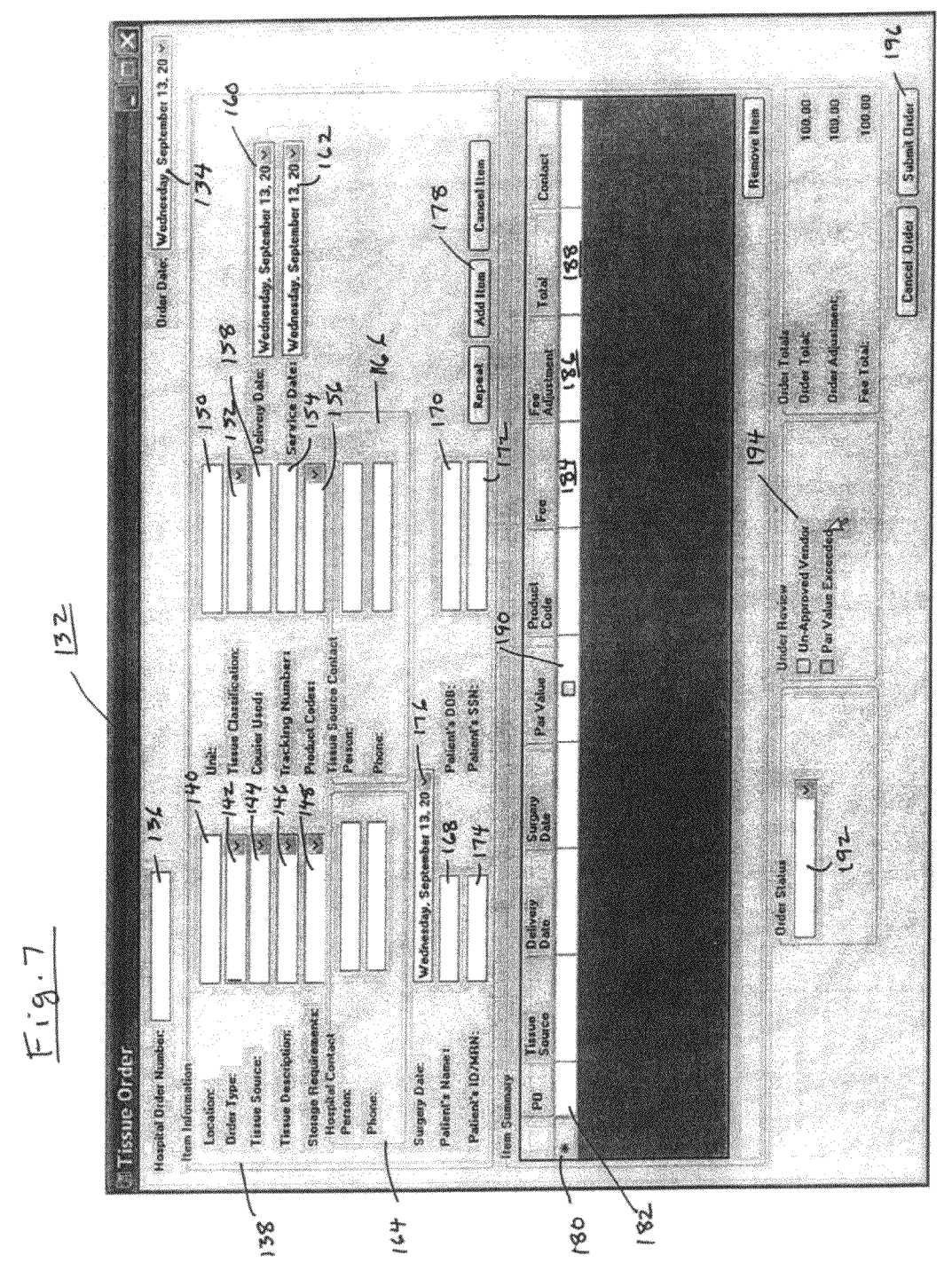

As further depicted in FIG. 7, the order date is recorded in field 134. A hospital order number will also be recorded in field 136. Specific identifying information for a piece of transplantable material is also noted in the "item information" field 138, such as the location of the hospital 140, order type of tissue selected from drop down box 142, tissue source (i.e., vendor name) selected from a drop down box 144, and tissue description selected from a drop down box 146. Any special storage requirements for the tissue product established by the vendor will be noted in dropdown box 148.

The use location of the specific unit within hospital is recorded in field 150, while the tissue classification is noted in drop down box 152. The tracking number and product codes for the tissue are recorded in fields 154 and 156, respectively. If a courier service will be used to deliver the ordered tissue product to the hospital, this fact should be noted in field 158. The required delivery date for the tissue product should be recorded in drop down box 160, while the date by which the tissue product should be received by staff members within the hospital will be identified by drop down box 162. A contact person and phone number at the hospital can be noted in field 164. A corresponding contact person and phone number for the tissue vendor should be recorded in field 166.

If the tissue product is being ordered for a particular patient at the hospital, as opposed to generally restocking the hospital's inventory for such tissue product, then this fact must be recorded so that when the tissue product is received by the hospital it is reserved for that patient. This important identifying information will include the patient's name 168, date of birth 170, social security number 172, and ID/Medical Record Number ("MRN") 174, as well as the scheduled date for the patient's surgery 176. Once all the information for the tissue product purchase order is entered by the user into tissue order GUI 132, the "add item" icon 178 is clicked in order to add the identifying information for that tissue product order to the "shopping cart" 180. The comprehensive tissue management system 10 will populate the entry data for this tissue product to include a purchase order number 182, the tissue source 144, delivery date 160, surgery date 176, product code 156, and contact person 166. The purchase fee 184 for that tissue product, any adjustment from that standard purchase price 186, and the total price 188 for that item are also clearly identified. Finally, the system will inform the user in "par value" field 190 if too little or too much of that tissue product is in the hospital's inventory in order to assist the user's purchasing decision.

The order status will be noted in drop down box 192. This system will also automatically check the vendor information supplied under GUI 84 to make sure that that vendor possesses the necessary current FDA registration, state license, and other accreditation credentials to supply the tissue product. If the vendor for the tissue purchase order does not possess these necessary credentials, or this information has not been entered into the system, then the "unapproved vendor" indicator 194 will be triggered. A message will be sent by the comprehensive tissue management system to a predetermined official within the hospital who must authorize the purchase of the tissue product from the unapproved vendor before the purchase transaction can be placed. Such special authorization might be justified in case of an emergency where a surgical patient is in the operating room waiting for the tissue product. Such a purchase from an unauthorized vendor should be abnormal. In this manner, the system helps to ensure as a general matter that the hospital purchases transplantable materials only from properly credentialed vendor institutions. Once all of the tissue products for the purchase order are added to item summary screen 180, the user clicks on "submit order" icon 196 to submit the purchase order to the vendor.

Next, all bone grafts 12 supplied by tissue bank 14 to hospital 16 in accordance with FIG. 3 should be logged in accordance with step 200. Part of this invention's system is to determine where in the hospital this should be done—i.e., the blood bank, central supply, or surgical department. This is determined by the skill of the staff, the availability of staff 24 hours a day, and the ability to monitor and maintain storage equipment and alarms. The invention requires that a specific policy and procedure be established regarding how the tissue pieces will be accepted from tissue bank 14, and which specific staff 202 will be responsible for logging in the tissue. The logging process includes a unique identification number for each piece of tissue (specially assigned where necessary), coupled with the expiration date and acceptable temperature range for each tissue product.

Figure 8:
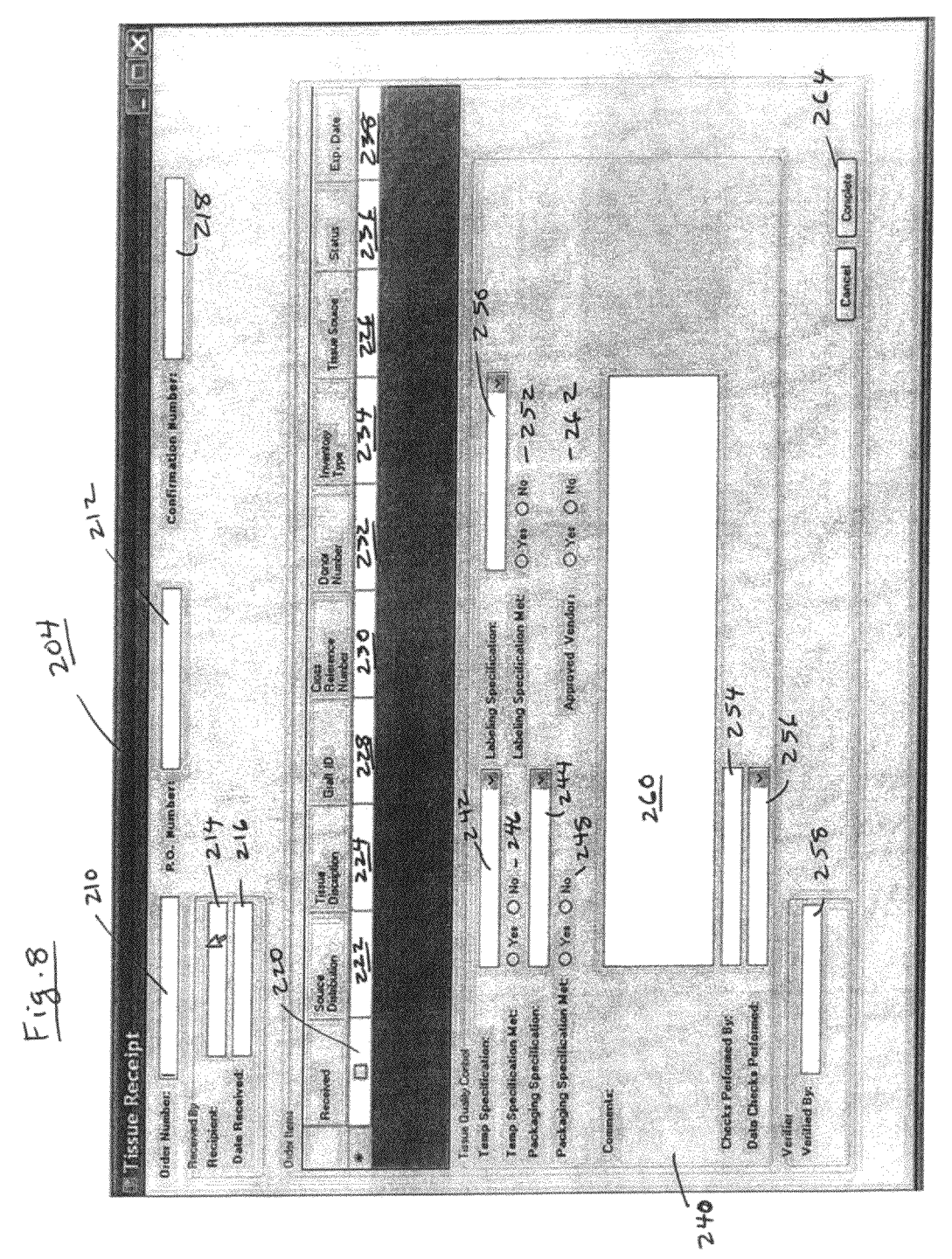

The tissue login procedure 200 conducted by the hospital staff 202 is assisted by the tissue receipt GUI 204 shown in FIG. 8. This screen of the software program 54 is accessed by means of clicking on the tissue processing icon 66 of the home page GUI 60 shown in FIG. 4. The section of this icon 66 will cause the software program to bring up the tissue processing GUI 206 shown in FIG. 9. By double clicking on the tissue login icon 208, the tissue receipt GUI 204 of FIG. 8 is produced by the computer.

The hospital order number 210 and purchase order number 212 fields of tissue receipt GUI 210 will automatically be populated by the system, using data inputted into the tissue order GUI 132 of FIG. 7. The hospital staff member who received delivery of the tissue product should input his or her name and the date into fields 214 and 216, respectively, along with the confirmation number 218 for the tissue product.

The computer system will automatically populate the GUI 204 to confirm that the tissue was received 220, along with tissue description 224, and tissue source 226 fields in the tissue receipt GUI 204 from the information previously entered into the tissue order GUI 132. The software program will also assign a unique graft identification 228 to the tissue product so that it can be identified throughout its custody by the hospital and ultimate implantation in a patient. Also assigned to assist in the identification of the piece of tissue is a cross-reference number 230. A donor number 232 identifies the specific donor of the specific piece of tissue. Inventory type 234 identifies if the tissue is for hospital stock, consignment, special order, or transfer and status 236 indicates the disposition of the tissue—e.g., discarded, implanted, quarantined, available, or reserved. The expiration date 238 identified by the vendor the piece of tissue is a critical piece of information that is also entered into GUI 204.

Other important information pertaining to the piece of tissue that should be entered into the tissue receipt GUI in field 240 is quality control information. This includes the vendor's temperature specifications 242 for this tissue product, and the packaging insert specifications 244. Following an inspection of the product, a confirmation should also be entered into the system in fields 246 and 248, respectively, whether or not the temperature specification and packaging specifications were actually satisfied at the time of receipt of the product. Labeling specifications 250 and whether those labeling specifications were met 252 should also be noted. Identification of the hospital staff member performing the tissue quality control inspection and the date of the inspection should be entered in fields 254 and 256. If desired, a verifier can be used to double check this information with the verifier identified in field 258. Additional written comments regarding the inspection results can be entered into field 260.

The system will automatically populate field 262 to indicate whether or not the vendor has been approved for purposes of supplying the transplantable material. Once the necessary information has been inserted into this tissue receipt GUI 204, clicking the "complete" icon 264 will cause the system to process the information.

In some cases, tissue sent to the surgery unit 20 that was not used within the surgical procedure may be returned to the storage location 18 for use by a future patient. The login step should address the login procedure for such returned tissue for re-issuance for future surgeries.

The invention requires the hospital to establish inspection criteria 239 (FIG. 3) for the incoming transplantable material. This process step includes verification upon receipt of the transplantable material product from the tissue bank 14 that package integrity of the tissue is satisfied to avoid infection or spoilage of the tissue. The staff member 202 should also verify that the temperature range for the piece of transplantable material during transport from tissue bank 14 was controlled and acceptable in accordance with FDA regulatory standards or the manufacture's recommendations.

The invention also requires the medical establishment to create specific policies and procedures regarding how it should handle, store, and transplant the transplantable material 12. This determination 270 (FIG. 3) begins with careful review and maintenance on file of the package inserts for each type of transplantable material used by the establishment. Each supplier of tissue has created different instructions for how their products should be transported, handled, stored reconstituted, and used. These instructions are approved by the FDA. Great care should be taken to ensure that the package integrity is maintained for the products during transportation and handling in order to avoid introduction of contaminants into the product.

The transplantable materials must also be maintained at their proper temperatures during their storage at ambient temperature or in refrigerators and freezers at the hospital. The FDA-approved package insert for each type of tissue product will specify the appropriate temperature or temperature range. The hospital must determine what types of refrigerator or freezer units it will use, along with the associated monitoring and alarm equipment. Appropriate policies and procedures 64 (FIG. 3) need to be established to ensure continuous monitoring of the temperature conditions in the refrigerator and freezer units with a central alarm system or chart recorder. A number of transplantable material products that are stored at ambient temperature do not specify the temperature range that needs to be maintained. The invention requires that the hospital create an appropriate temperature range. If not specified, the invention suggests careful review of the package inserts for the ambient temperature products used by the hospital. The range is then created by taking the highest low temperature identified in the package inserts and the lowest high temperature designated in these inserts.

Alarms for each storage unit should be set so that the alarm sounds before the temperature within the unit exceeds the predetermined temperature range. In this manner, the ambient storage area, refrigerator or freezer units will maintain a temperature condition that accommodates the transplantable materials stored within.

Schedules for the periodic inspection and maintenance of the refrigerator and freezer storage units must be created. Periodic testing of the alarm systems operatively connected to the storage units and the emergency power source should also be scheduled. It is also important to maintain daily records of the actual storage unit temperature conditions to prove that the transplantable materials, in fact, were stored at their required conditions. Each piece of transplantable material should be identified within the log record by its unique identifier number, date, time and storage or handling location to document its exact condition until final disposition, transplant or discard.

If the surgery unit 20 maintains its own storage units for transplantable materials, then it must establish similar policies and procedures for monitoring the temperature conditions therein, inspecting the valid operating conditions thereof, and documenting the actual temperature conditions of the refrigerator and freezer units. The surgical unit 20, however, must also maintain precise records for each and every piece of transplantable material that it handles and uses in surgical procedures. Such records should identify the specific piece of transplantable material, its condition and all reagents or other supplies introduced to it prior to its transplantation or implantation into the patient.

Another important step carried out by staff within the surgical unit 20 will be the reconstitution of the transplantable material from its storage condition to a condition necessary for its use in surgery. This is determined by the package insert and current good medical practice. This will typically include the immersion of the tissues, like bone, into a sterile saline bath with or without antibiotics. Other human cells, tissues and organs are reconstituted with appropriate reagents. The nurse or other qualified/trained staff member designated to conduct such reconstitution step must carefully read and adhere to the specific instructions printed in the package insert for the transplantable material product and make the implanting surgeon aware that they are deviating from the FDA-approved package insert. The surgeon decides based on his medical judgment whether the change from the package insert is merited. At the end of the surgical procedure, the tissue usage identification cards ("TUIC") GUI 460 shown in FIG. 16 must be completed for the product implanted into the patient and promptly returned to tissue bank 14.

In some cases, a hospital 16 may actually serve as a supplier of transplantable materials to other medical establishments. This often is the case for "sister" hospitals or large hospitals that internally source transplantable materials and use them in their other surgical procedures. The comprehensive tissue management system 10 requires the hospital 16 to periodically ask itself these questions:

Does it produce human cells, tissue and cellular and tissue-based products ("HCT/Ps"), including stem cells, reproductive cells, tissue or surgical bone?

Does it store purchased tissue and ship it to another institution that is not part of its organization? For example, does it supply a VA Medical Center or other hospital within the community?

Does it store tissue from one patient case on the chance that the surgeon needs it for another patient with the exception of vessels used in organ transplant?

Does it perform additional processing on incoming tissue? For example, gas sterilization of bone for further use.

Does its testing lab perform tissue donor testing for communicable diseases?

Does its lab test specimens for organ donors, and are such results used to determine eligibility for tissue donors?

If the answer to any of these questions during this source facility regulatory compliance step 280 depicted in FIG. 3 is "yes," then the hospital 16 must register itself with the FDA much like a tissue bank 14 does.

A critical component for the comprehensive tissue management method 26 of the present invention is the hospital staff 202. As shown in FIG. 3, a trained staff member must be designated with responsibility for each of the process steps described above. Every effort must be made to ensure that the responsible staff member has the required educational background 205 (FIG. 3) for conducting the process step. Also important is ensuring that such staff members will actually be available at the relevant time to carry out the activity step. For example, if transplantable material is maintained in a surgical unit and the responsible person unavailable to respond to an alarm sounding on a refrigerator unit this undermines proper operation of the comprehensive tissue management system 26 FIG. 3. All designated staff members should be provided the necessary training 206 to discharge their responsibilities. They should also be provided the necessary policies and procedures 207 by hospital management that allows them to perform their duties without risk to themselves or the patient.

In order to ensure that the above-described process steps are carried out, the comprehensive tissue management system 10 should be embodied with a record-keeping system that requires the completion of individual records 208 attesting to the completion of the individual process steps. The comprehensive tissue management system 10 is preferably embodied within a computer tissue tracking and tracing software system. Individual screen shots for a process step could require completion of the necessary data entry before the computer can progress to the next screen shot.

Finally, a periodic internal audit 209 must be conducted by the hospital 16 for all of the process steps that form the acquisition and storage components 26 of the comprehensive tissue management system 10. Only in this manner can the hospital management be assured that their staff is complying with the necessary policies and procedures, and take corrective action where necessary.

Figure 10:
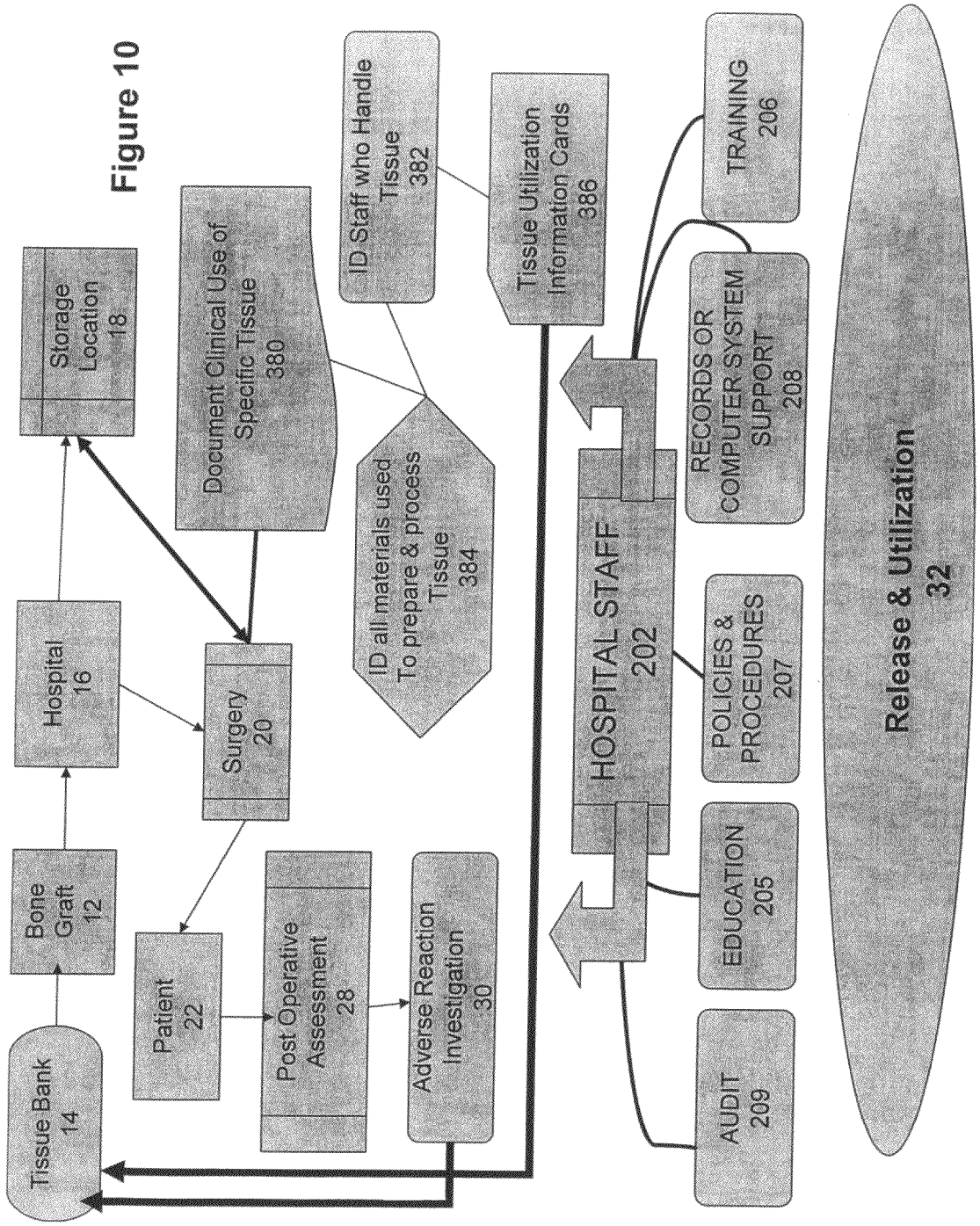
FIG. 10 is a schematic diagram showing the release and utilization portion of the comprehensive tissue management system.

FIG. 10 illustrates the tissue tracing portion 32 of the comprehensive tissue management system in greater detail. The objective of this system is to provide an adequate record of the transplantable material's history in case of an adverse reaction 30 in patient 22 after surgery or, if the tissue bank issues a recall and the patient who receives the transplantable material needs to be identified. For example, if the adverse reaction is an infection and is due to the operative contamination or the management of the bone graft in the hospital, then the problem is localized to the hospital and can be addressed by improving the hospital's practices. If, on the other hand, the infection is determined by investigation 30 to have been caused by the tissue graft, then the tissue needs to be traced back to tissue bank 14, so the supplier can be warned. A recall of similar transplantable material supplied by tissue bank 14 to the hospital 16 and other medical establishments may be necessary. In some cases, follow up diagnostic and medical treatment of other patients who were implant recipients of the similar transplantable material may be warranted as well.

To monitor the history of the tissue during its life in the hospital requires documentation of multiple steps starting with its entrance in the hospital and its maintenance in the storage locality 18 (FIG. 3). This will include assigning a unique identification code to the bone graft products, confirming the package integrity and safe condition of the bone graft upon receipt from the tissue bank 14, recording the actual temperature conditions, and identifying all staff members who handle the bone graft and the date and time of any such possession or handling activities from the time of initial login until the bone graft is transported to the surgical unit 20 for use in a surgery. Many of the process steps described above for the acquisition and storage tracking portion 26 of the comprehensive tissue management system can be employed to support the documentation steps.

Once the transplantable material 12 reaches the hospital 16 and is logged in, it will be maintained in any of a number of possible storage locations 18 in the hospital before it is transported to the surgical unit 20 for clinical use in a patient 22. Possible storage locations at the hospital include the blood bank, central storage department and the surgical unit.

Figure 9:
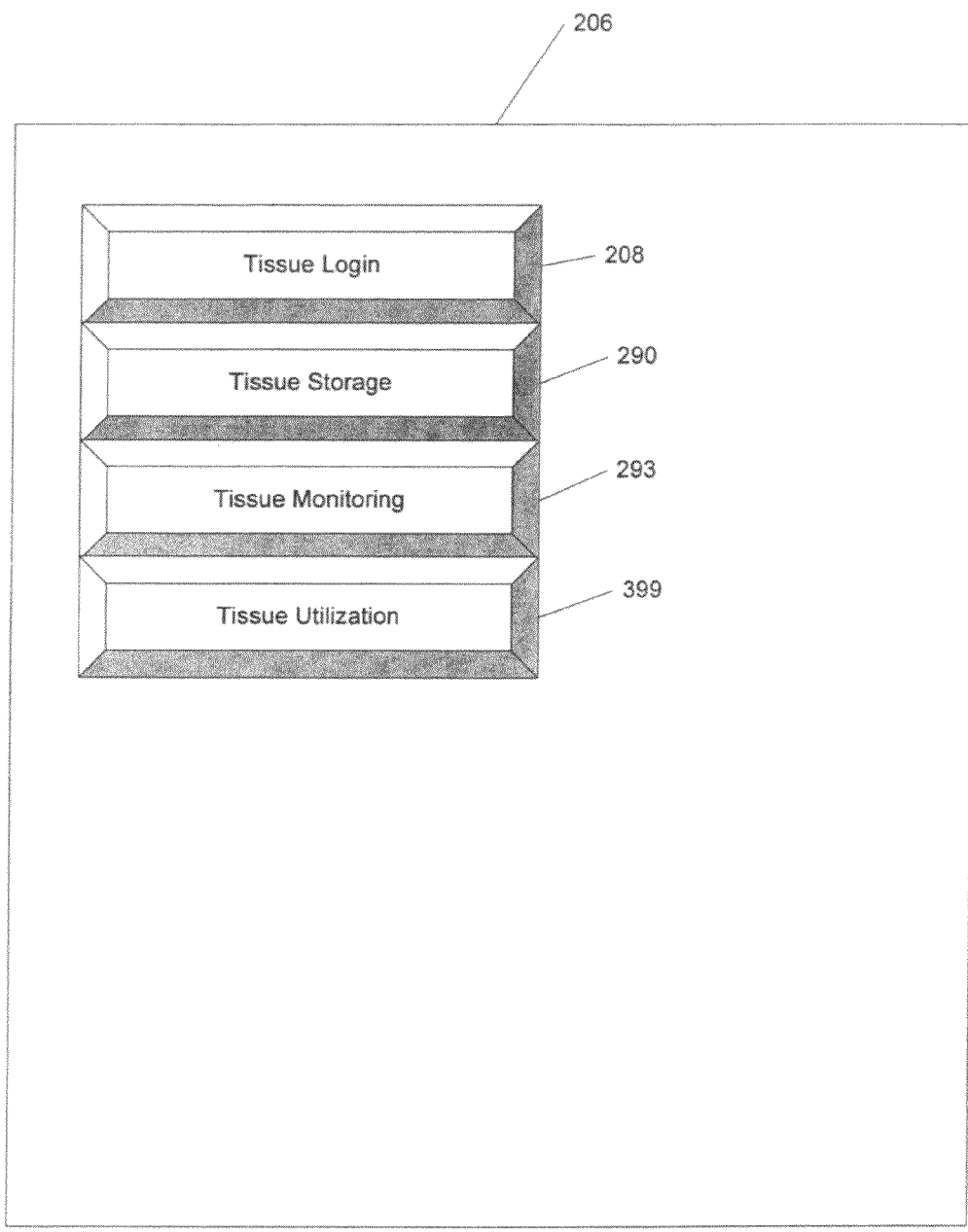
FIG. 9 is an interactive graphic user interface illustrating a tissue processing screen.
Figure 11:
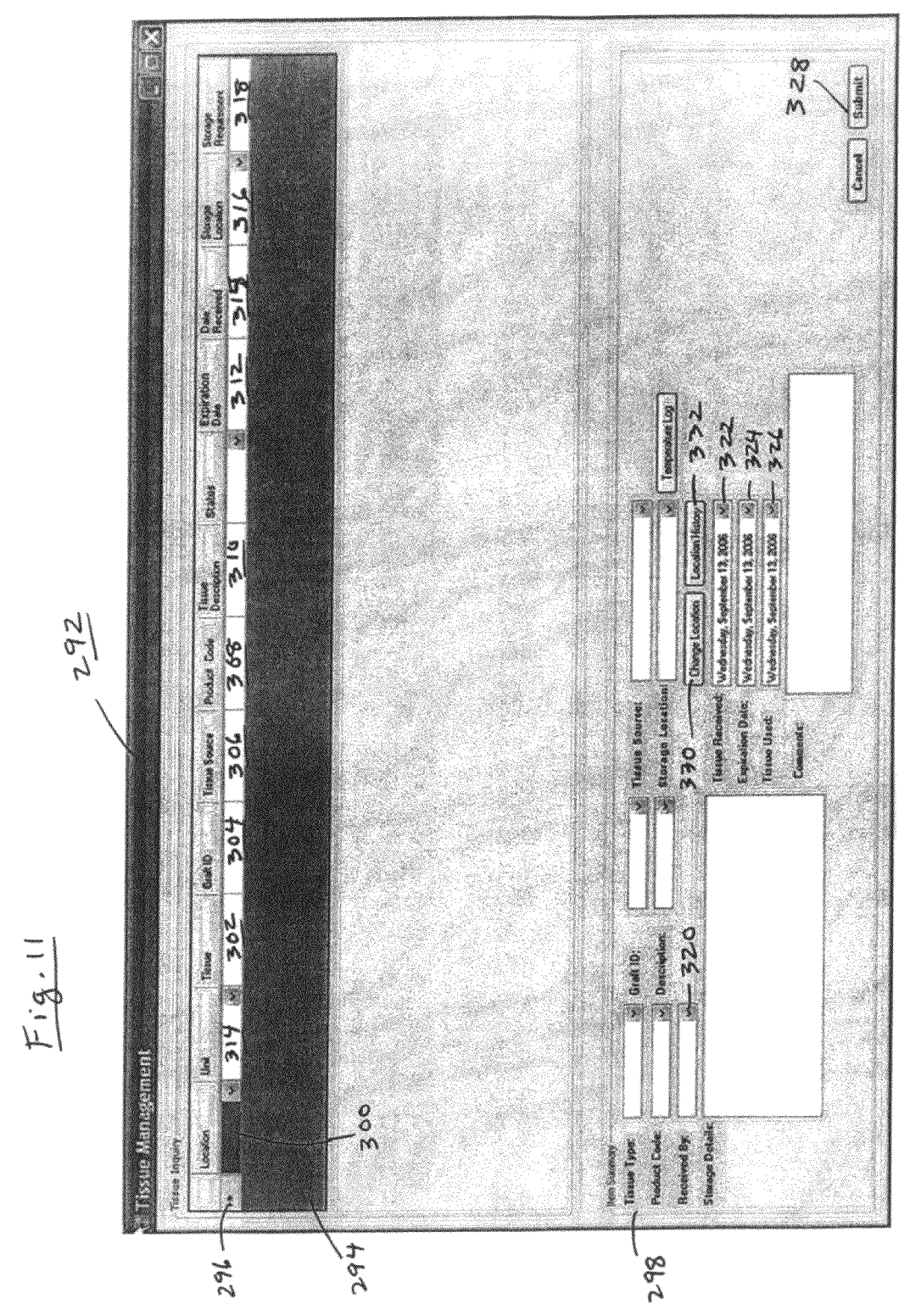

By selecting tissue storage icon 290 of tissue processing GUI 206 of FIG. 9, the computer system will call up tissue management GUI 292 shown in FIG. 11. This GUI contains a tissue inquiry window 294 that lists all of the pieces of tissue that have been logged into the system. Selection of a given tissue entry 296 will highlight its status and location information in the item summary 298 in the bottom portion of the GUI 292. The software system will automatically populate data for the tissue from data entered into prior GUI's. Such data includes the hospital location 300, tissue classification (e.g. musculoskeletal, cardiovascular, skin) 302, graft ID number 304, tissue vendor source 306, product code 308 received from the manufacturer, and a description 310 of the particular tissue, such as "30 cc of crushed cancellous." The expiration date 312 and receipt date 315 will also be automatically entered into GUI 292. Each time the tissue piece is transported within the hospital 16, the staff member must update the unit field 314 (e.g., Blood Bank) and storage location field 316 (e.g., Refrigerator 3) to identify the exact location of the tissue piece. The required storage requirements for the tissue piece should also be entered into field 318 for easy reference by the staff member responsible for Refrigerator 3 in the hospital's Blood Bank.

The name of the staff member who received the tissue in its present storage location should also be entered into field 320 along with its storage receipt date 322. The expiration date for the tissue piece will be monitored in field 324. The actual date on which the tissue piece was used in a surgical procedure should also be recorded in field 326. In this manner, storage location data for the tissue piece can be submitted for further processing by the tissue management system by clicking the "submit" icon 328.

A piece of tissue will receive separate entries within tissue management GUI 292 for each time that it is transported to a new storage location. Selection of the "change location" icon 330 will cause the software system to call up change location GUI 334, shown in FIG. 12. This change tissue location GUI allows the user to insert a new storage location from a drop down menu in field 336. The specific date 337 and time 338 of the transfer are also recorded, along with the user's name or initials in field 340. This change tissue location GUI also enables the user to specifically record a special status of the tissue piece. This could include return of the tissue piece to the vendor 342 in the event, e.g., the tissue is no longer need, there is a recall by the vendor, or if the tissue was determined by the hospital's quality control inspection to be defective. It could also include discarding of the tissue 344 after, e.g., its expiration date has passed, or quarantining of the tissue inside the hospital 346 in the event of an adverse reaction investigation where safety of a similar piece of tissue is under review.

In this manner, the related tissue will not be used in a surgical procedure until it is cleared. When tissue is used by the hospital in a surgical procedure, this will be recorded in the "issued" field 348. Selection of icon 350 allows this change tissue location data to be submitted for further processing by the software program 54.

Figures 12, 13:
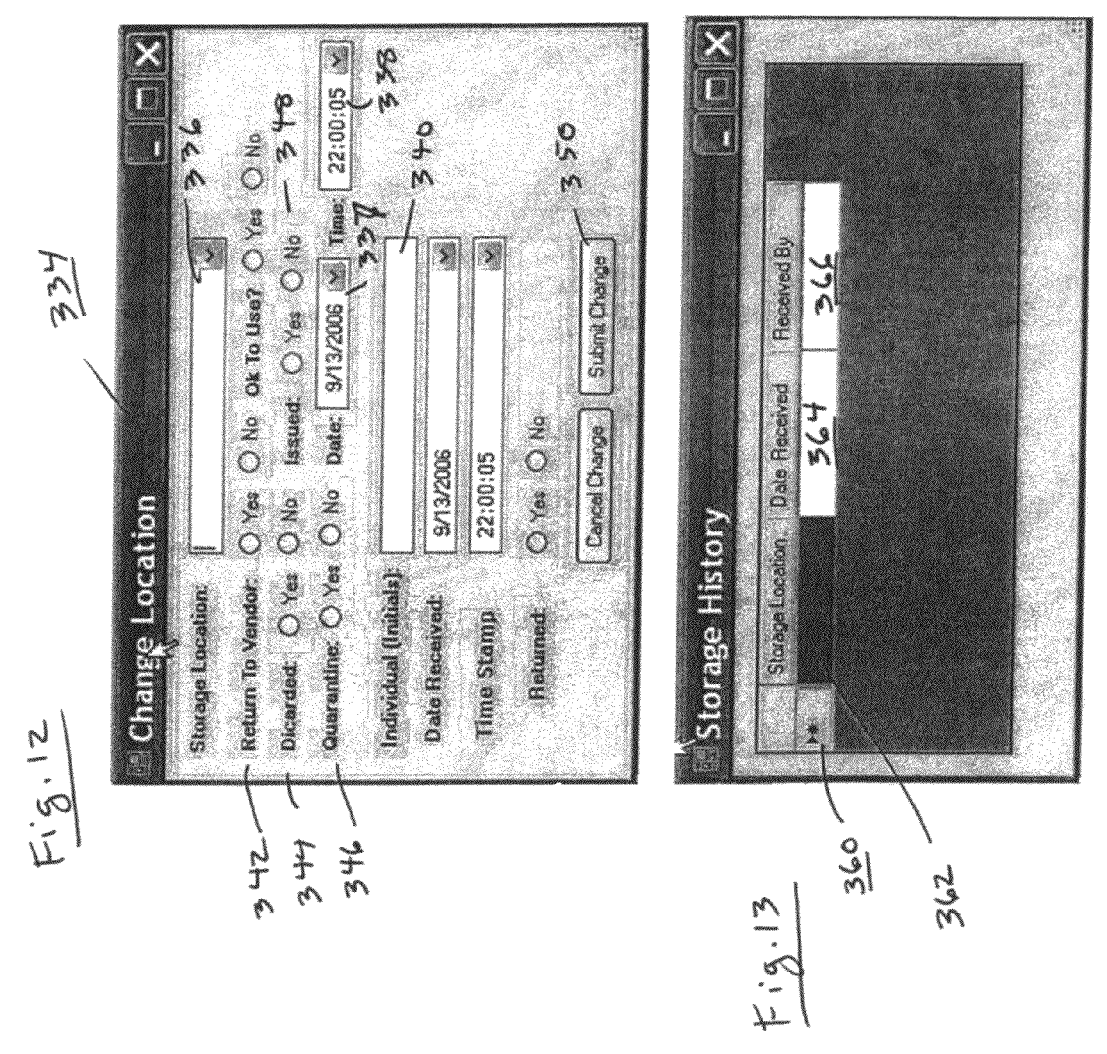

Selection of the "location history" icon 332 of the tissue management GUI 292 of FIG. 11 will call forth the storage history GUI 360 shown in FIG. 13. This GUI screen provides a succinct history for a particular piece of tissue selected from the tissue index of GUI 292. It sets forth each storage location 362 for the tissue piece, along with the transfer date 364 and staff member 366 receiving the transferred tissue piece. A separate row of data will appear in GUI 360 for each time that the tissue piece was transferred inside the hospital. This historical record enables the hospital's handling of the tissue piece to be traced in the event of an adverse reaction investigation or vendor tissue recall. This is an important feature of the release and utilization portion 32 of the comprehensive tissue management system 10 of the present invention.

Once the transplantable material 12 reaches the surgical unit 20, thorough records need to be created concerning the clinical use 380 (FIG. 10) of this specific bone graft. This includes identification of the staff member who accepts the bone graft, identification of all surgical staff members involved in preparing the bone graft for its use in the surgical procedure, and recording the dates, times and personnel for all such activities, as set forth in tissue handling staff identification step 382.

An important processing step by the surgical unit is the reconstitution of the bone graft product prior to its implantation in patient 22. As previously described, this should be done strictly in accordance with the instructions on the package insert. Documentation should be produced pursuant to step 384 to indicate what supplies like syringes, heparin, saline or basins were actually used to reconstitute or prepare the bone graft, and confirm that all such supplies were used prior to their indicated expiration dates.

An identification of all staff members, including the surgeon, who handle, prepare and implant the bone graft should be recorded, including the date and times of such activities in accordance with step 382. At the end of the surgical procedure, the tissue usage information card should be completed pursuant to step 386 and returned to tissue bank 14 to provide additional documentation of the clinical use and disposition of bone graft 12 in patient 22. Specific policies and procedures need to be established to determine who will complete these cards according to the tissue bank requirement, since completion and return of such tissue usage information cards is frequently overlooked within the hospital industry.

The essential element of the release and utilization portion 32 of the comprehensive tissue management system 10 of the present invention is thorough and concurrent record keeping. Failure to document important steps in the acceptance, handling, storage, transportation, processing and clinical use of the tissue and associated reagents will greatly undermine the integrity of the system and put the patient at risk. Likewise, documentation of the necessary information at a point in time substantially after the acceptance, handling, storage, transportation, processing, or surgery activity will call into question the accuracy and validity of the system.

Figure 14:
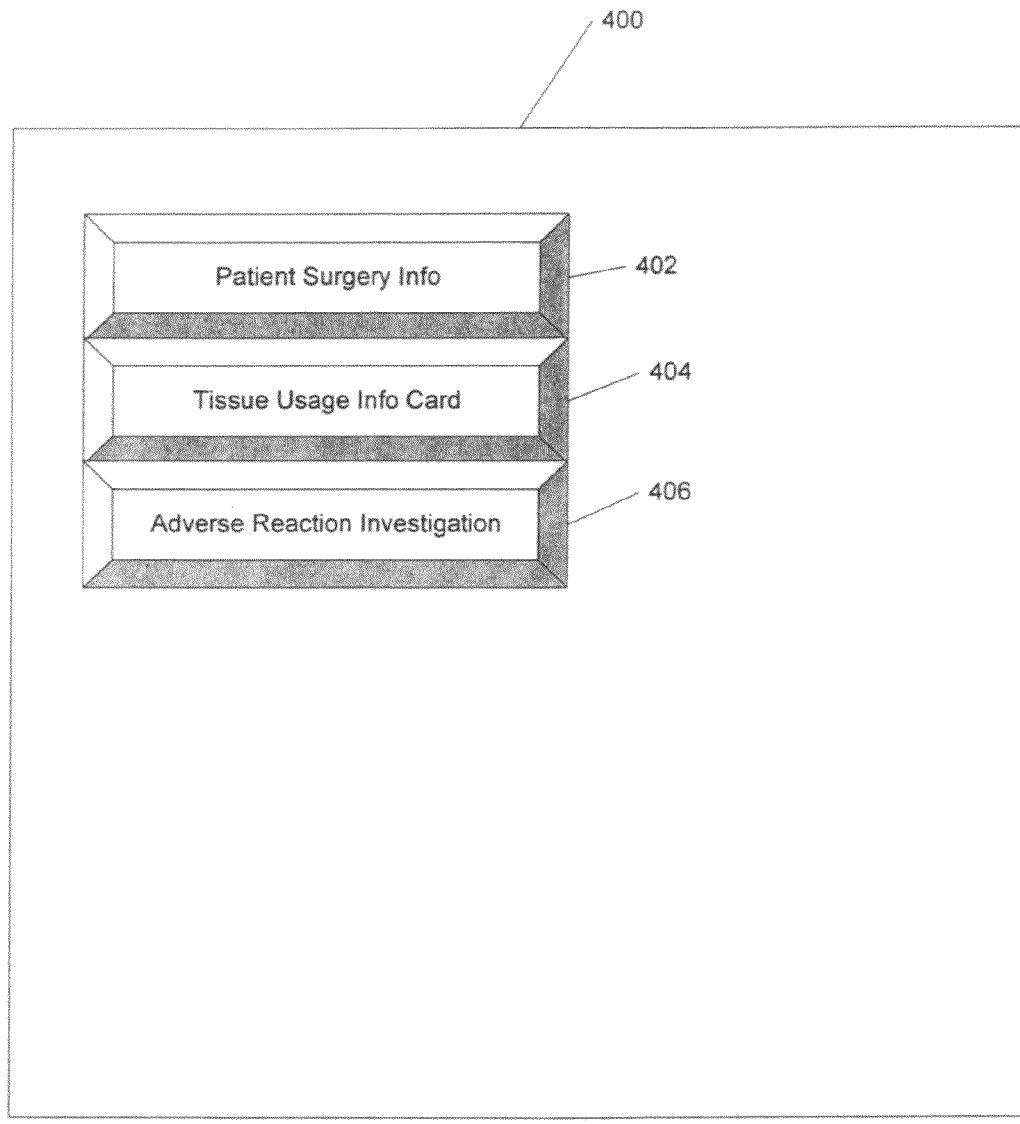
FIG. 14 is an interactive graphic user interface illustrating a tissue utilization menu screen.
Figure 15:
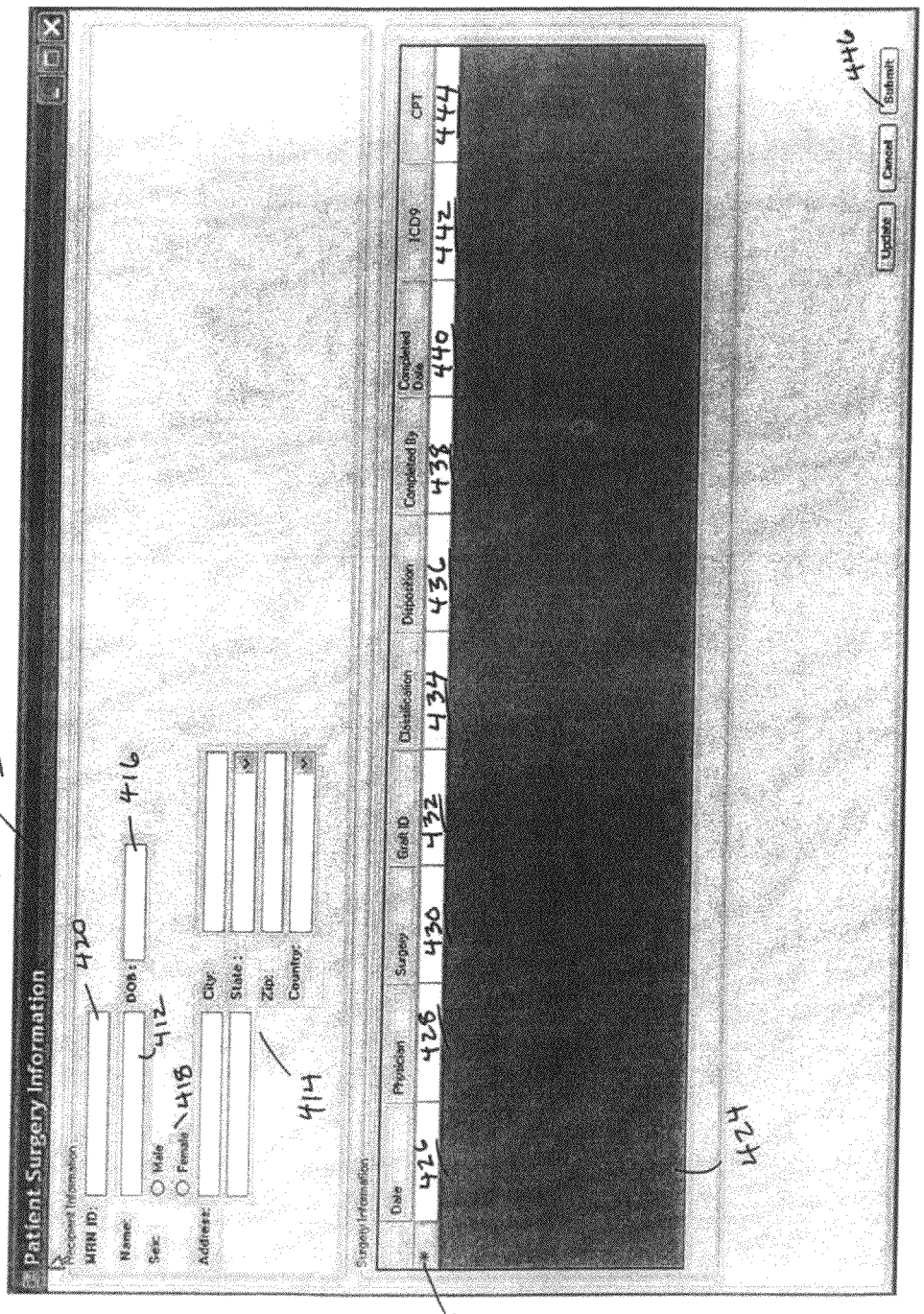
FIG. 15 is an interactive graphic user interface illustrating a patient surgery information screen.

Clicking on "tissue utilization" icon 399 of tissue processing GUI 206 shown in FIG. 9 calls up surgical use GUI 400 shown in FIG. 14. This, in turn, permits the user to select "patent surgery info" icon 402, which will cause the software 54 of comprehensive tissue management system 10 to call forth patent surgery information GUI 410 depicted in FIG. 15.

In this patient surgery information GUI 410, a staff member should enter relevant information for the patient 22 who receives the bone graft 12 during surgery 20. Pursuant to the documentation of the clinical use of the specific tissue 380, this information includes the name of the patient 412, the patient's address 414, and date of birth 416. The gender 418 of the patient and his or her medical record number (MRN) ID 420 are also inputted.

A patient may receive more than one surgery at the hospital. Therefore, each tissue implanted is represented by a row 422 within the surgery information field 424 of GUI 410. Each such implant is documented in terms of its date 426, physician 428, and surgical procedure 430. Also identified is the unique graft ID number 432 for the specific tissue piece implanted into the patient, along with its classification 434 and disposition (either transplanted or discarded) 436. The staff member completing this record 438 and date of its completion 440 are also inserted into GUI 410. The billing codes ICD9 442 and CPT 444 should also be included. The "submit" icon 446 may be clicked to cause the comprehensive tissue management system 10 to further process this data.

Figure 16:
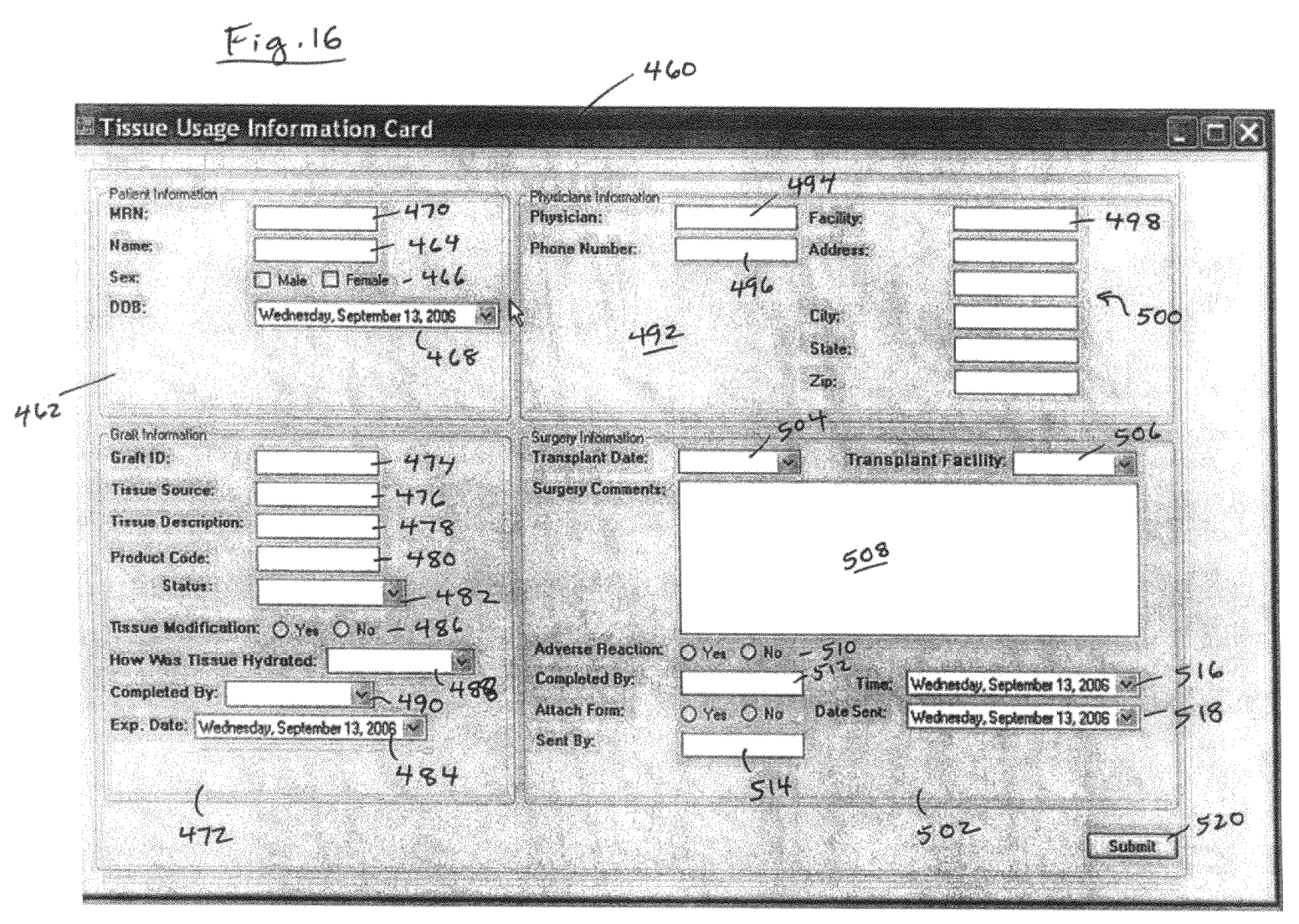

GUI 460 for producing a tissue usage information card 386 is shown in FIG. 16. This GUI is accessed within the comprehensive tissue management system 10 by clicking on "tissue usage information card" icon 404 in surgical use GUI 400 shown in FIG. 14. This card is sent to tissue bank 14 after the surgery to inform the tissue bank that the bone graft 12 that it supplied to hospital 16 was implanted into patient 22.

The information within patient information field 462 is automatically populated by the system from information inputted previously into the patient surgery information GUI 410. This includes the patient's name 464, gender 466, date of birth 468, and MRN 470. Likewise, much of the graft information 472 is automatically populated by the system from information previously inserted into the tissue management GUI 292, including the graft ID 474, tissue source 476, tissue description 478, product code 480, status 482, and tissue expiration date 484. Special information concerning whether the tissue was modified 486, and how it was hydrated in preparation for the surgery 488 should be inserted into GUI 460 with the hospital staff member who completed this information being identified within field 490.

The physician's information field 492 for the surgical procedure includes identification of the physician's name 494, phone number 496, name of the hospital facility 498, and its address information 500.

Finally relevant information for the surgical procedure is inputted into surgery information field 502. Such information includes the transplant or implant date 504, surgical facility 506, any special comments concerning the surgery recorded within field 508, and whether or not an adverse reaction 510 within the patient 22 was discovered. The hospital staff member completing this portion of the tissue usage information card must be identified within field 512. Similarly, the staff member who actually sends the tissue usage information card to the tissue bank should be identified within field 514, along with the time 516 and date 518 of the transmission. Clicking on the "submit" icon 520 will cause the tissue management system 10 to process this information to produce the tissue usage information card.

The hospital 16 should establish the time period for retention of each record within portion 32 of the comprehensive tissue management system 10. In the case of login sheets and recorded procedures for the transplantable material, such records should be maintained for at least 10 years. Any records related to the transplantable material like tissue usage information cards, preparation materials, central alarm/chart recorders must be kept 10 years after the date of distribution, transplant or expiration date of the material in question, whichever is latest.

A procedure for version control must also be established for all procedures that affect the transplantable material, including a unique name for each procedure, a version number and date when it became effective, and when the previous version no longer applies in order to keep the documentary records and procedure requirements clear.

As described previously for the portion 26 of the comprehensive tissue management system 10, designated hospital staff members 202 that are part of the release and utilization portion 32 of the system need to be assigned responsibility for keeping and maintaining all records and other documents associated with the comprehensive tissue management system (see FIG. 10). While a requisite degree of education 205 may be helpful, character traits of conscientiousness and thoroughness, as well as available time may be more helpful for any such staff member. All designated staff members should also be provided adequate training 206 in such tasks as how to read temperature charts, inspect refrigeration or freezer storage units, confirm the instructions on transplantable material product insert sheets, etc. These hospital staff members 202 should also be provided understandable policies and procedures 207 to help them do their part to support the integrity and accuracy of the comprehensive tissue management system 10. Periodic internal and external audits 209 should be scheduled by hospital management to confirm that all of the necessary steps pursuant to the comprehensive tissue management system are accomplished.

The comprehensive tissue management system 10 is predicated upon the proposition that hospital management and staff will actively investigate adverse reaction 30 and take corrective action in response to any adverse reaction in a patient 22. To accomplish thorough investigations of adverse reactions the invention has created the concept of "Medical Cladistics." Cladistics is the branch of biology that determines evolutionary and taxonomic relationships between organisms based on derived similarities. Similarly, medical cladistics looks for derived similarities in investigation of clinical problems such as adverse reactions so appropriate risk categories can be created. For example, if a patient develops an infection following surgery in which tissue has been used, and an investigation shows that other patients were operated on in the same operating room ("OR") suite developed similar infections, the "risk clade" is the OR suite, not the transplantable material, or the OR staff and the equipment sterilizer.

If a transplantable material product was associated with an infection, then the risk clade would have to be identified. Some transplantable material products can be more harshly treated than others. For example, tendons do not receive the same sterilizing treatments used by some tissue processors for bone. If an infection due to the transplantable material were bacterial and the transplantable material product implicated was a tendon, than the risk clade would be the other tendons from the same donor, not necessarily the bone products. If the infection were hepatitis, than all products from the donor may be the risk clade.

Investigation of the risk clade involves both the hospital where the transplantable material was transplanted and the transplantable material processor. Therefore, the transplantable material supplier must be notified immediately and a full investigation of the donor and processing quality control methods would be necessary to resolve the case.

The process of identifying a risk clade begins by defining an adverse reaction. This requires thorough evaluation of the actual orthopedic or other clinical and surgical practices employed by the hospital and its physicians. Factors that may influence adverse reactions include:

Physician preference for certain proprietary transplant material products and supplies. Some products carry greater risks than others.

How such products are normally prepared within the hospital.

Pre and post-operative antibiotics that are commonly used by the surgical team.

Are tissue products soaked in antibiotics prior to their implantation?

Incidence of infections in the hospital comparing allograft versus metallic devices.

Does the surgeon perform a gram stain or culture of the tissue product prior to its implantation?

Determining whether adverse reaction in a patient is based upon cultures, symptoms, or both.

The hospital 16 must establish policies and procedures to reinforce the prompt investigation and reporting of adverse reactions to answer the following questions:

Who within the hospital's management is responsible for receiving information concerning adverse events revealed during the post-operative assessment 28 (see FIG. 1)?

How are these events to be documented? (e.g. evaluation, report, log, etc.).

Who is responsible for determining if the adverse event was secondary to the tissue implant?

Who notifies the tissue bank and receives their evaluation and report?

Who is responsible for requesting additional information and testing, and for completing the investigation?

What other transplant materials received from the tissue bank 14 need to be traced and quarantined within the hospital 16?

All adverse event records need to be periodically reviewed for completeness.

Who will report the investigation conclusions to the clinician?

In the event that the tissue bank reports that the transplantable material was the cause of the adverse reaction, or is otherwise contaminated, then the hospital must have in place established policies and procedures for quarantining all impacted transplantable materials stored within the hospital's inventory. Such procedures encompass the ability to trace such transplantable materials, notification of the patient's physician if the transplantable material was already transplanted, maintenance of a report or log that accounts for all such transplantable material products, and an identification of a department and specific staff members responsible for doing so.

Patients who have received a transplant from donors who subsequently are found to have HIV, HTLV-I/II, viral hepatitis, or other infectious agents known to be transmittable by tissue must also be identified and informed of infectious risks. This includes donors who have donated more than one time, such as donors of reproductive tissue, stem cells, and surgical bones. When such a donor is found to have a confirmed positive test for infectious agents, then all previous donations of transplantable materials need to be identified via the release and utilization portion 32 of the comprehensive tissue management system 10, and a determination of which donations could have occurred while the donor was within the window period for this infectious agent must be made. The hospital's procedures in cooperation with the supplier should include:

Who is responsible for identifying all previous donations?

Who is responsible for determining which previous donations are at risk?

How should all subsequent recipients of the infected transplant material from this donor be identified?

How should all such recipients be notified?

Who is responsible for counseling the recipients of the infected transplant material?

Is there a policy for follow-up testing of the recipients?

Is notification of the state health department or other regulatory agencies required?

Is there a procedure and log to document all of this information?

Is the individual who counsels the recipients properly educated and trained?

Figure 17:
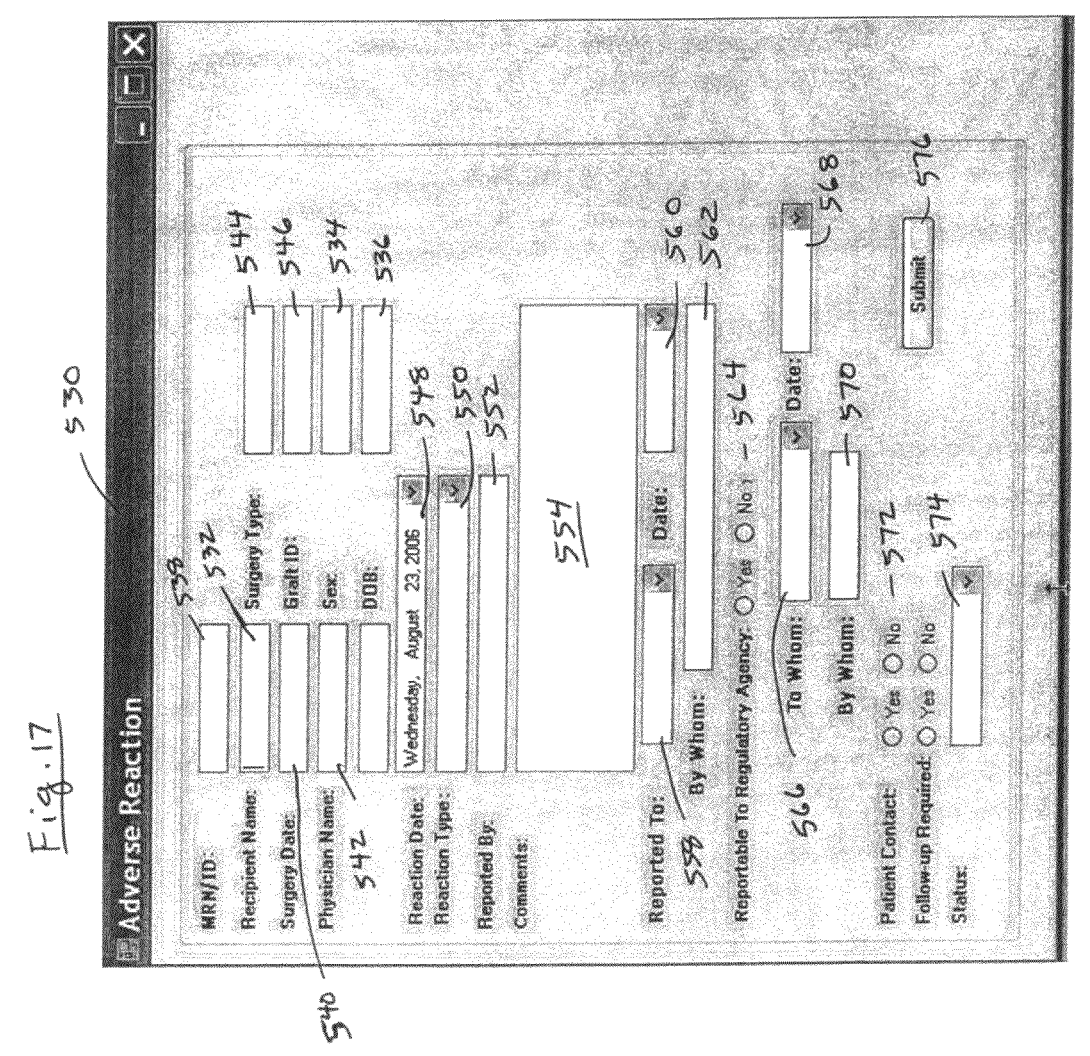

The adverse reaction investigation GUI 530 of the comprehensive tissue management system 10 is depicted FIG. 17. This GUI is accessed by the user by clicking on "adverse reaction investigation" icon 406 in GUI 400 shown in FIG. 14. Once the patient has been identified by MRN/ID or name, the system will automatically populate many fields of this adverse reaction records screen from information that was previously inputted into prior GUI screens, including the patient 532 who received the tissue product, the patient's gender 534, and date of birth 536, MRN/ID 538, surgery date 540, physician's name 542, type of surgery 544, and graft ID 546 for the specific tissue product implanted in the surgery.

Next, the date on which the adverse reaction occurred 548, reaction type 550, the staff member who reported it 552, and summary comments to describe further the adverse reaction 554 are inputted into GUI 530. Also important to note within the record created by GUI 530 is the hospital manager to whom the adverse reaction was reported 558, the date on which the report was made 560, and the identity of the staff member who reported it 562.

In some cases, occurrence of the adverse reaction may need to be reported to a regulatory agency. This fact should be noted in field 564, along with identification of the specific regulatory agency 566, date 568, and the reporting hospital staff member 570 when this further report is made.

Finally, a determination whether further clinical or psychological treatment is required for the patient suffering from the adverse reaction should be recorded in field 572 and the status 574 of that follow up. Clicking on the "submit" icon 576 causes the system to process the information inputted into GUI 530. In this manner, the comprehensive tissue management system 10 of the present invention creates an accurate record of the adverse reaction investigation 30 that prompts appropriate follow-up by the hospital's staff member 202 with regard to the patient 22, tissue bank 14, and regulatory authorities.

In its simplest embodiment, the comprehensive tissue management system 10 of the present invention may be a paper record keeping system. This may be particularly appropriate for relatively small medical establishments that do not handle and process enough transplantable materials to justify the cost of a computer-based system. The requirements established by the medical establishment for filling out and completing such paper forms and submitting them to appropriate managers may be sufficient for ensuring that the various processing steps for handling, storage, reconstitution, and surgical use of the transplantable material by staff members are being conducted in a manner compliant with prevailing regulations and industry standards, and that a thorough document record is produced therefore. However, it is important to incorporate within such policies and procedures safeguards for ensuring that all of these internal requirements are met by staff members in a compliant and timely manner. This could include a requirement that records be filled out from one processing step before the next processing step for the transplantable material can be conducted by the same or another staff member. Periodic internal and external audits will also be important for assuring compliance.

However, the computer software system disclosed within this application for the comprehensive tissue management system 10 provides the most reliable method for providing a comprehensive information system concerning clinical usages of transplantable materials, and prompting hospital staff members to appropriately handle, store, process, transport, reconstitute, and use the transplantable material. Moreover, such a computer software-based system enables a user easily and quickly to search for desired information. Furthermore, such a computer system can readily compile the information to produce reports that can be used to manage and regulate clinical use of the transplantable materials.

The computer system can also notify those monitoring the tissue of any of the steps described above by visual and/or audible means. Continual electronic monitoring of the transplantable material allows the computer system to store and display the entire history of a particular transplantable material sample. The continual monitoring reduces the risks that the transplantable material sample's integrity has been compromised.

Adequate policies and procedures adopted by the medical establishment can help with assuring that staff members are using the computer-based system in a compliant and timely manner. Periodic internal and external audits will also be helpful.

The above specifications and drawings provide a complete description of the structure and operation of the comprehensive tissue management system for acquisition and storage 26 of transplantable material and release and utilization 32 of transplantable material under the present invention. However, the invention is capable of use in various other combinations, modifications, embodiments, and environments without departing from the spirit and scope of the invention. Therefore, the description is not intended to limit the invention to the particular form disclosed, and the invention resides in the claim and hereinafter appended.

We claim:

1. A tissue management system incorporating a database of information, processor, and software program containing an organized set of instructions for tracking the internal processing by a medical establishment of a piece of transplantable material provided by a supplier for subsequent transplantation or implantation into a patient, such system comprising:
    (a) means for assigning a unique identification code to the transplantable material upon its receipt by the medical establishment from the supplier;
    (b) means for prompting an inspection of the transplantable material upon its receipt from the supplier for an unsafe condition;
    (c) a comprehensive set of standard operating procedures adopted by the medical establishment covering at least one step for login, handling, storage conditions, reconstitution, or surgical use of the transplantable material by staff members of the medical establishment in a manner compliant with prevailing safety regulations and industry mandates;
    (d) means for entering into the database required data concerning how the at least one step for the login, handling, storage conditions, reconstitution or surgical use of the transplantable material by the staff member was carried out;
    (e) means for processing such entered data by the software program which is built upon the standard operating procedures to ensure that the step for the login, handling, storage conditions, reconstitution, or surgical use of the transplantable material was conducted strictly in a manner compliant with the standard operating procedures before the next step for the login, handling, storage conditions, reconstitution, or surgical use of the transplantable material can be undertaken by the staff members;
    (f) means for prompting the assessment of the patient after transplantation or implantation of the transplantable material for evidence of an adverse effect;
    (g) means for prompting the investigation of any such adverse effect discovered in the patient to determine whether it constitutes an adverse reaction; and
    (h) means for reporting any such adverse reaction to the supplier that supplied the transplant material to the medical establishment;
    (i) wherein the transplantable material is chosen from the group consisting of human cells, tissue, or organs intended for implantation, transplantation, infusion, or transfer to a patient, including, but not limited to: musculoskeletal tissues like bone, tendons, fascia, ligaments, cartilage, and bioengineered bone products; skin; cardiovascular tissues like heart valves, arteries, veins, and pericardium; reproductive cells like sperm, semen, oocytes, fertilized eggs, and embryos; cellular therapies like stem cells, progenitor cells, cord blood, chondrocytes, bone marrow, and neural cells; dura mater; breast milk; eyes, corneas; organs; islet cells; parathyroids; autologous tissue; and synthetic and xenographic tissue used as replacements for human tissue; as well as non-biologic implants, including but not limited to: titanium screws; titanium or carbon-fiber cages or resorbable cages, fixation systems, saline or silicone breast implants, synthetic polymers, prosthetic hips, knees and other joint combinations thereof; as well as surgical instruments, equipment, reagents, and supplies associated with the transplanting or implanting of any transplant material into a patient; and
    (j) wherein the medical establishment is an organization directed to the storage, research, transplantation, or implantation of transplantable materials chosen from the group consisting of hospitals, medical clinics, surgical centers, fertility clinics, tissue banks, organ banks, organ donor banks, university and research facilities, diagnostic laboratories, and willed body programs.

2. The tissue tracking management system of claim 1 further comprising means for designating one or more staff members of the medical establishment with specific responsibility for conducting each of the means for elements (a-b and d-h).

3. The tissue tracking management system of claim 1 further comprising means for prompting a certification verification that the supplier currently possesses all required regulatory certifications and licenses to supply the transplantable material.

4. The tissue tracking management system of claim 1 further comprising means for prompting an evaluation of any safety or health risks posed by transplantable materials supplied by the supplier against the benefits provided by such transplantable material.

5. The tissue tracking management system of claim 1 further comprising means for ensuring that a staff member of the medical establishment who performs any of the means for elements (a-b and d-h) possesses a relevant educational background for performing such step.

6. The tissue tracking management system of claim 1 further comprising means for ensuring that relevant training is provided to a staff member of the medical establishment who performs any of the means for elements (a-b and d-h).

7. The tissue tracking management system of claim 1, wherein the information contained within the database comprises data regarding the supplier.

8. The tissue tracking management system of claim 1, wherein the information contained within the database comprises the storage conditions of the transplantable material.

9. The tissue tracking management system of claim 1, wherein the information contained within the database comprises clinical data concerning the patient.

10. The tissue tracking management system of claim 1, wherein the information contained within the database comprises clinical data concerning the transplant or implant surgery.

11. The tissue tracking management system of claim 1 further comprising means for placing an order with the supplier for a piece of transplantable material.

12. A tissue management system incorporating a database of information, processor, and software program containing an organized set of instructions for tracing a piece of transplantable material received by a medical establishment from a supplier throughout the internal life of the transplantable material within the medical establishment until it is transplanted or implanted into a patient, such system comprising:
  (a) means for assigning a unique identification code for the transplantable material upon its receipt by the medical establishment from the supplier;
  (b) means for documenting into the database by a staff member data for the completion of each processing step comprising login, handling, storage conditions, reconstitution, or surgical use applied by staff members to the transplantable material;
  (c) means for documenting in the database the present location of the transplantable material within the medical establishment;
  (d) means for documenting in the database the identity of each staff member who comes into contact with the transplantable material;
  (e) means for documenting in the database the date and time of each step applied to the transplantable material;
  (f) means for documenting in the database all materials used to prepare and process the transplantable material;
  (g) means for documenting in the database the unique identification code of the transplantable material transplanted or implanted into the patient;
  (h) a comprehensive set of standard operating procedures adopted by the medical establishment covering the data that must be recorded to adequately describe the steps for the login, handling, storage conditions, reconstitution, or surgical use of the transplantable material carried out by staff members of the medical establishment with respect to the transplantable material
  (i) means for processing such entered data by the software program which is built upon the standard operating procedures to make sure that at least one of the documentation steps (b-g) complies with the documentation requirements under the standard operating procedures before the next step for the login, handling, storage conditions, reconstitution, or surgical use of the transplantable material can be undertaken by the staff members;
  (j) means for tracing the transplantable material back to the supplier that supplied it to the medical establishment or to the specific login, handling, storage conditions, reconstitution, or surgical use processing step applied by a staff member of the medical establishment to the transplantable material;
  (k) wherein the transplantable material is chosen from the group consisting of human cells, tissue, or organs intended for implantation, transplantation, infusion, or transfer to a patient, including, but not limited to: musculoskeletal tissues like bone, tendons, fascia, ligaments, cartilage, and bioengineered bone products; skin; cardiovascular tissues like heart valves, arteries, veins, and pericardium; reproductive cells like sperm, semen, oocytes, fertilized eggs, and embryos; cellular therapies like stem cells, progenitor cells, cord blood, chondrocytes, bone marrow, and neural cells; dura mater; breast milk; eyes; corneas; organs; islet cells; parathyroids; autologous tissue; and synthetic and xenographic tissue used as replacements for human tissue; as well as non-biologic implants, including but not limited to: titanium screws, titanium or carbon-fiber cages or resorbable cages, fixation systems, saline or silicone breast implants, synthetic polymers, prosthetic hips, knees and other joint combinations thereof; as well as surgical instruments, equipment, reagents, and supplies associated with the transplanting or implanting of any transplant material into a patient; and
  (l) wherein the medical establishment is an organization directed to the storage, research, transplantation, or implantation of transplantable materials chosen from the group consisting of hospitals, medical clinics, surgical centers, fertility clinics, tissue banks, organ donor banks, university and research facilities, diagnostic laboratories, and willed body programs.

13. The tissue tracing management system of claim 12 further comprising means for designating one or more staff members of the medical establishment with specific responsibility for conducting each of the means for elements (a-g and j).

14. The tissue tracing management system of claim 12 further comprising means for sending to the supplier a tissue utilization information card for the transplantable material transplanted or implanted to the patient.

15. The tissue tracing management system of claim 12, wherein the tracing means for element (j) is conducted in response to an adverse reaction detected in the patient into whom the transplantable material was transplanted or implanted.

16. The tissue tracing management system of claim 15 further comprising means for notifying the supplier that supplied the transplantable material to the medical establishment of the adverse reaction in the patient.

17. The tissue tracing management system of claim 12, wherein the tracing means for element (j) is conducted in response to a warning received from the supplier that supplied the transplantable material to the medical establishment.

18. The tissue tracing management system of claim 12 further comprising means for ensuring that a staff member of the medical establishment who performs any of the means for elements (a-g and j) possesses a relevant educational background for performing such step.

19. The tissue tracing management system of claim 12 further comprising means for ensuring that relevant training is provided to a staff member of the medical establishment who performs any of the means for elements (a-g and j).

20. The tissue tracing management system of claim 12, wherein the information contained within the database comprises data regarding the supplier.

21. The tissue tracing management system of claim 12, wherein the information contained within the database comprises the storage conditions of the transplantable material.

22. The tissue tracing management system of claim 12, wherein the information contained within the database comprises clinical data concerning the patient.

23. The tissue tracing management system of claim 12, wherein the information contained within the database comprises clinical data concerning the transplant or implant surgery.

24. The tissue tracing management system of claim 12 further comprising means for reporting a list of certified suppliers of transplantable material.

25. The tissue tracing management system of claim 12 further comprising means for reporting the certification credentials of a particular supplier.

26. The tissue tracing management system of claim 25, wherein such certification credential is selected from the group consisting of Food & Drug Administration registration, American Association of Blood Banking accreditation, American Association of Tissue Banks ("AATB") accreditation, Eye Bank Association of America ("EBAA") accreditation, and licensure within a relevant geographic region.

27. The tissue tracing management system of claim 12 further comprising means for reporting results of an audit conducted by the medical establishment upon the supplier.

28. The tissue tracing management system of claim 12 further comprising means for reporting an order placed for the purchase of transplantable material.

29. The tissue tracing management system of claim 12 further comprising means for reporting a quality inspection assessment of transplantable material received from the supplier.

30. The tissue tracing management system of claim 12 further comprising means for reporting the present location of transplantable material within the medical establishment.

31. The tissue tracing management system of claim 12 further comprising means for reporting the storage history within the medical establishment of a piece of transplantable material.

32. The tissue tracing management system of claim 12 further comprising means for reporting results of the adverse reaction investigation with regard to a piece of transplanted material.

\* \* \* \* \*